US009125891B2

(12) United States Patent
Lagasse

(10) Patent No.: US 9,125,891 B2
(45) Date of Patent: Sep. 8, 2015

(54) LYMPH NODES AS A SITE FOR REGENERATION

(75) Inventor: Eric Lagasse, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 148 days.

(21) Appl. No.: 12/921,001

(22) PCT Filed: Mar. 9, 2009

(86) PCT No.: PCT/US2009/036506
§ 371 (c)(1),
(2), (4) Date: Sep. 3, 2010

(87) PCT Pub. No.: WO2009/111778
PCT Pub. Date: Sep. 11, 2009

(65) Prior Publication Data
US 2011/0002899 A1 Jan. 6, 2011

Related U.S. Application Data

(60) Provisional application No. 61/068,548, filed on Mar. 7, 2008.

(51) Int. Cl.
A61K 35/12 (2015.01)
A61K 35/39 (2015.01)
A61K 35/26 (2015.01)
A61K 35/407 (2015.01)

(52) U.S. Cl.
CPC ............ *A61K 35/39* (2013.01); *A61K 35/26* (2013.01); *A61K 35/407* (2013.01)

(58) Field of Classification Search
None
See application file for complete search history.

(56) References Cited

U.S. PATENT DOCUMENTS

| 6,797,264 | B1 | 9/2004 | Eriksson |
| 7,211,404 | B2 | 5/2007 | Lagasse et al. |
| 2002/0182188 | A1 | 12/2002 | Reid et al. |
| 2007/0087029 | A1 | 4/2007 | Pakala |
| 2011/0002899 | A1 | 1/2011 | Lagasse |

FOREIGN PATENT DOCUMENTS

| EP | 0 830 146 | | 3/2010 |
| WO | WO2004/003142 | * | 1/2004 |
| WO | WO2008/055354 | * | 5/2008 |

OTHER PUBLICATIONS

Yamanaka, Induction of pluripotent stem cells from mouse fibroblasts by four transcription factors, Cell Prolif., 2008, pp. 51-56, vol. 41, No. Suppl. 1.
Yang et al., Epithelial-Mesenchymal Transition: At the Crossroads of Development and Tumor Metastasis, Developmental Cell, Jun. 2008, pp. 818-829, vol. 14.
Alves et al., Slug is overexpressed in gastric carcinomas and may act synergistically with SIP I and Snail in the down-regulation of E-cadherin, J Pathol, 2007, pp. 507-515, vol. 211.
Anderson et al., T cell adhesion to endothelium: the FRC conduit system and other anatomic and molecular features which facilitate the adhesion cascade in lymph node, seminars in Immunology, 1993, pp. 271-282, vol. 5.
Andrian, Intravital Microscopy of the Peripheral Lymph Node Microcirculation in Mice, Microcirculation, 1996, pp. 287-300, vol. 3, No. 3.
Andrian et al., Homing and Cellular Traffic in Lymph Nodes, Nature Reviews: Immunology, Nov. 2003, pp. 867-878, vol. 3.
Barralet et al., Tissue Engineering of Human Biliary Epithelial Cells on Polyglycolic Acid/Polycaprolactone Scaffolds Maintains Long-Term Phenotypic Stability, Tissue Engineering, 2003, pp. 1037-1045, vol. 9, No. 5.
Basma et al., Differentiation and Transplantation of Human Embryonic Stem Cell-Derived Hepatocytes, Gastroenterology, 2009, pp. 990-999, vol. 136.
Borenstein et al., Microfabrication of Three-Dimensional Engineered Scaffolds, Tissue Engineering, 2007, pp. 1837-1844, vol. 13, No. 8.
Demetriou et al., Replacement of Liver Function in Rats by Transplantation of Microcarrier-Attached Hepatocytes, Science, Sep. 12, 1986, pp. 1190-1192, vol. 233, No. 4769.
Fisher et al., Human Hepatocyte Transplantation: Worldwide Results, Transplantation, Aug. 27, 2006, pp. 441-449, vol. 82, No. 4.
Fuller, Transplantation of isolated hepatocytes: A review of current ideas, Journal of Hepatology, 1988, pp. 368-376, vol. 7.
Girard et al., High endothelial venules (HEVs): specialized endothelium for lymphocyte migration, Immunology Today, 1995, pp. 449-457, vol. 16, No. 9.
Gretz et al., Cords, channels, corridors and conduits: critical architectural elements facilitating cell interactions in the lymph node cortex, Immunological Reviews, 1997, pp. 11-24, vol. 156.
Grompe et al., Pharmacological correction of neonatal lethal hepatic dysfunction in a murine model of hereditary tyrosinaemia type I, Nature Genetics, Aug. 1995, pp. 453-460, vol. 10.
Grompe et al., Therapeutic trials in the murine model of hereditary tyrosinaemia type I: A progress report, J. Inher. Metab. Dis. 1998, pp. 518-531, vol. 21.
Grompe, Principles of therapeutic liver repopulation, J Inherit Metab Dis, 2006, pp. 421-425, vol. 29.
Guha et al., Amelioration of Radiation-induced Liver Damage in Partailly Hepatectomized Rats by Hepatocyte Transplantation, Cancer Research, Dec. 1, 1999, pp. 5871-5874, vol. 59.
Guha et al., Normal Hepatocytes Correct Serum Bilirubin After Repopulation of Gunn Rat Liver Subjected to Irradiation/Partial Resection, Hepatology, Aug. 2002, pp. 354-362, vol. 36, No. 2.

(Continued)

*Primary Examiner* — Michail Belyavskyi
(74) *Attorney, Agent, or Firm* — Baker Botts L.L.P.

(57) ABSTRACT

Methods of transplanting cells, such as hepatocytes, are presented herein. Such methods are useful for treating liver disease as well as other disorders.

19 Claims, 22 Drawing Sheets

(56) References Cited

OTHER PUBLICATIONS

Gupta et al., Hepatocytes Exhibit Superior Transgene Expression after Transplantation into Liver and Spleen Compared with Peritoneal Cavity or Dorsal Fat Pad: Implications for Hepatic Gene Therapy, Human Gene Therapy, Aug. 1994, pp. 959-967, vol. 5.

Gupta et al., Therapeutic potential of hepatocyte transplantation, seminars in Cell & Developmental Biology, 2002, pp. 439-446, vol. 13.

Habibullah, Hepatocyte Transplantation: Need for Liver Cell Bank, Tropical Gastroenterology, 1992, pp. 129-132, vol. 13, No. 4.

Hamazaki et al., Microencapsulated Multicellular Spheroid of Rat Hepatocytes Transplanted Intraperitoneally after 90% Hepatectomy, Hepato-Gastroenterology, Nov.-Dec. 2002, pp. 1514-1516, vol. 49, No. 48.

Henne-Bruns et al., Intraperitoneal hepatocyte transplantation: morphological results, Virchows Archiv A Pathol Anat, 1991, pp. 45-50, vol. 419.

Ifkovits et al., Review: Photopolymerizable and Degradable Biomaterials for Tissue Engineering Applications, Tissue Engineering, 2007, pp. 2369-2388, vol. 13, No. 10.

Ishida et al., Ductular morphogenesis and functional polarization of normal human biliary epithelia cells in three-dimensional culture, Journal of Hepatology, 2001, pp. 2-9, vol. 35.

Kang et al., Epithelial-Mesenchymal Transitions: Twist in Development and Metastasis, Cell, Aug. 6, 2004, pp. 277-279, vol. 118.

Knox, Enzymes Involved in Conversion of Tyrosine to Acetoacetate, Biochem J., 1951, pp. 287-300, vol. 2.

Knox et al., Homogentisate Oxidase of Liver, www.jbc.org, Dec. 4, 1954, pp. 479-487.

Laconi et al., Long-Term, Near-Total Liver Replacement by Transplantation of Isolated Hepatocytes in Rats Treated with Retrorsine, American Journal of Pathology, Jul. 1998, pp. 319-329, vol. 153, No. 1.

Lagasse et al., Purified hematopoietic stem cells can differentiate into hepatocytes in vivo, Nature Medicine, Nov. 2000, pp. 1229-1234, vol. 6, No. 11.

Li et al., Isolation and Culturing of Hepatocytes from Human Livers, J. Tiss. Cult. Meth., 1992, pp. 139-146, vol. 14.

Liotta et al., The microenvironemnt of the tumour-host interface, Nature, May 17, 2001, pp. 375-379, vol. 411.

Mai et al., Treatment of fulminant liver failure by transplantation of microencapsulated primary or immortalized xenogeneic hepatocytes, Xenotransplantation, 2005, pp. 457-464, vol. 12.

Mehigan et al., Disseminated Intravascular Coagulation and portal Hypertension Following Pancreatic Islet Autotransplantation, 1979, pp. 287-293, J.B. Lippincott Company.

Miyasaka et al., Lymphocyte Trafficking Across high Endothelial Venules: Dogmas and Enigmas, Nature, May 2004, pp. 360-370, vol. 4.

Muller et al., Involvement of chemokine receptors in breast cancer metastasis, Nature, Mar. 1, 2001, pp. 50-60, vol. 410.

Nakagawa et al., Generation of induced pluripotent stem cells without Myc from mouse and human fibroblasts, Nature Biotechnology, Jan. 2008, pp. 101-106, vol. 26, No. 1.

Nakashima et al., In situ tissue engineering of the bile duct using polypropylene mesh-collagen tubes, The International Journal of Artificial Organs, 2007, pp. 75-85, vol. 30, No. 1.

Ochoa et al., Developing a Core Platform for the Tissue Engineering of Vital Organs, Transplantation Reviews, Oct. 2001, pp. 184-199, vol. 15, No. 4.

Ohashi et al., Sustained survival of human hepatocytes in mice: A model for in vivo infection with human hepatitis B and hepatitis delta viruses, Nature Medicine, Mar. 2000, pp. 327-331, vol. 6, No. 3.

Ohashi et al., Liver Tissue Engineering at Extrahepatic Sites in Mice as a Potential New Therapy for Genetic Liver Diseases, Hepatology, 2005, pp. 132-140, vol. 41, No. 1.

Overturf et al., Hepatocytes corrected by gene therapy are selected in vivo in a murine model of hereditary tyrosinaemia type I, Nature Genetics, Mar. 1996, pp. 266-273, vol. 12.

Overturf et al., Serial Transplantation Reveals the Stem-Cell-Like Regenerative Potential of Adult Mouse Hepatocytes, American Journal of Pathology, Nov. 1997, pp. 1273-1280, vol. 151, No. 5.

Seglen, Hepatocyte Suspensions and Cultures as Tools in Experimental Carcinogenesis, Journal of Toxicology and Environmental Health, 1979, pp. 551-560, vol. 5, No. 2-3.

Sivertsen et al., Expression of Snail, Slug and Sip1 in malignant mesothelioma effusions is associated with matrix metalloproteinase, but not with cadherin expression, Lung Cancer, 2006, pp. 309-317, vol. 54.

Smith et al., Hypoxia leads to necrotic hepatocyte death, Journal of Biomedical Materials Research Part A, 2006, pp. 520-529.

Smith et al., Delivery of Hepatotrophic Factors Fails to Enhance Longer-Term Survival of Subcutaneously Transplanted Hepatocytes, Tissue Engineering, 2006, pp. 235-244, vol. 12, No. 2.

Taub, Liver Regeneration: From Myth to Mechanism, Nature Reviews: Molecular Cell Biology, Oct. 2004, pp. 836-847, vol. 5.

Tse et al., Mechanisms of Metastasis: Epithelial-to-Mesenchymal Transition and Contribution of Tumor Microenvironment, Journal of Cellular Biochemistry, 2007, pp. 816-829, vol. 101.

Umehara et al., Improved Survival and ammonia metabolism by intraperitoneal transplantation of microencapsulated hepatocytes in totally hepatectomized rats, Surgery, Sep. 2001, pp. 513-520, vol. 130, No. 2.

Walsh et al., Portal hypertension, hepatic infarction, and liver failure complicating pancreatic islet autotransplantation, Surgery, Apr. 1982, pp. 485-487, vol. 91, No. 4.

Komori et al., "The mouse lymph node as an ectopic transplantation site for multiple tissues", Nat. Biotechnol., 30(10):976-983 (2012).

International Search Report and Written Opinion for PCT/US2014/021420, dated Jun. 26, 2014.

* cited by examiner

Fig. 2A Fig. 2B
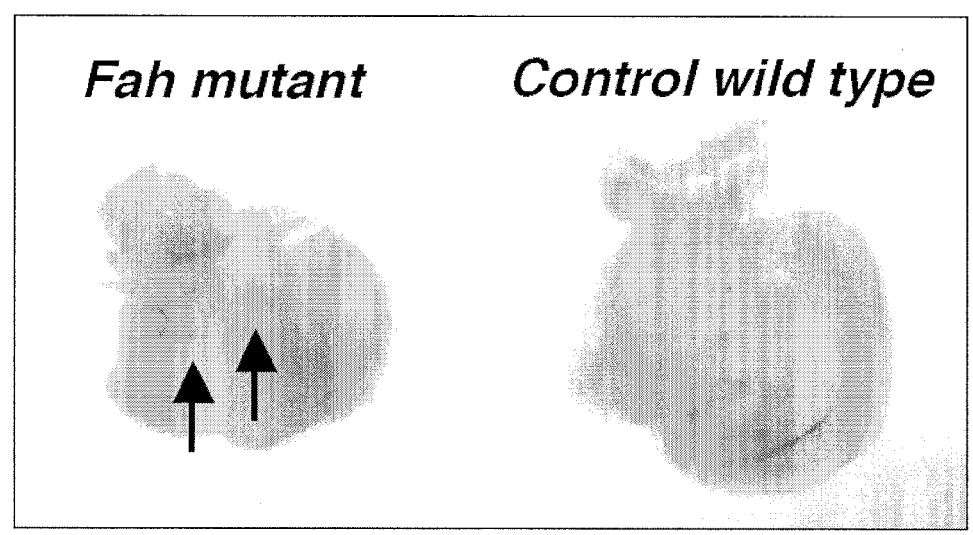
Fig. 2C

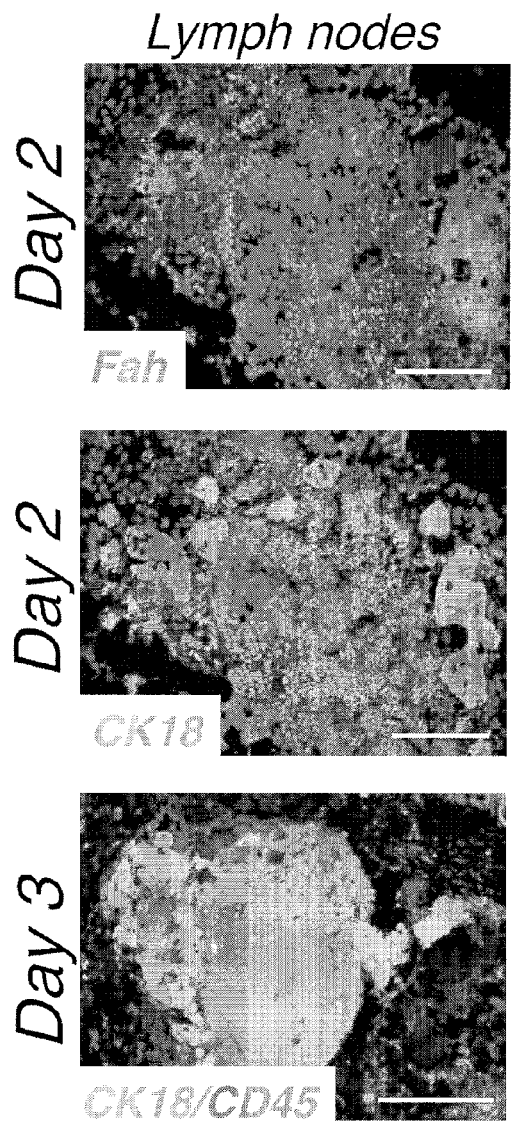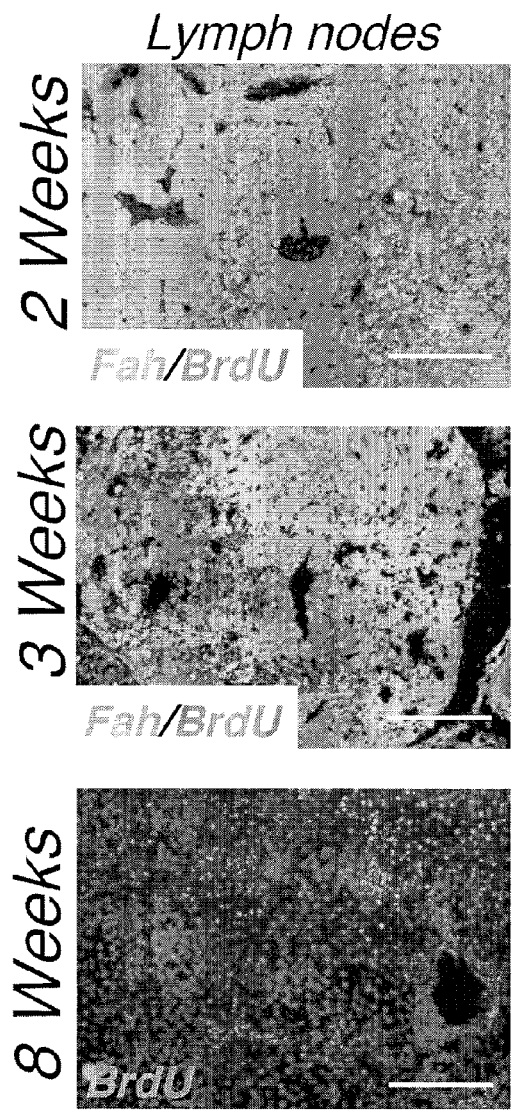
Fig. 12A
Fig. 12B

```
                          SEQUENCE LISTING

<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 1
ggaagcccaa ctatagcgag c                                                   21

<210> SEQ ID NO 2
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 2
cagttgaaga tcttccgcga c                                                   21

<210> SEQ ID NO 3
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 3
gcactgtgat gcccagtcta                                                     20

<210> SEQ ID NO 4
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 4
agcagccaga ctcctcatgt                                                     20

<210> SEQ ID NO 5
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 5
gtccatgcga actgccatct gatccgctct                                          30

<210> SEQ ID NO 6
<211> LENGTH: 20
```

```
<212> TYPE: DNA
<213> ORGANISM: Artificial
<220> FEATURE:
<223> OTHER INFORMATION: Synthetic Oligonucleotide

<400> SEQUENCE: 6
ggcttgcaga atctcgccac                                                    20

<210> SEQ ID NO 7
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 7
cgagaagctt ggagaatat                                                     19

<210> SEQ ID NO 8
<211> LENGTH: 18
<212> TYPE: DNA
<213> ORGANISM: Artificial
<220> FEATURE:
<223> OTHER INFORMATION: Synthetic Oligonucleotide

<400> SEQUENCE: 8
gtcagagcag agaagcat                                                      18

<210> SEQ ID NO 9
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 9
tggagaagag ctatgagctg c                                                  21

<210> SEQ ID NO 10
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 10
gatccacatc tgctggaagg                                                    20
```

LYMPH NODES AS A SITE FOR REGENERATION

CROSS REFERENCE TO RELATED APPLICATIONS

This application is a National Stage of International Application No. PCT/US2009/036506, filed Mar. 9, 2009, which in turn claims the benefit of U.S. Provisional Application No. 61/068,548, filed Mar. 7, 2008, which is incorporated herein by reference in its entirety.

BACKGROUND

Over 43,000 individuals die of a liver disease each year. Although the causes of liver disease are varied, the result, end-stage liver disease, where the liver ceases to function, will lead to the patient's death without intervention. Often, the only option is a liver transplant. However, there is a chronic shortage of donor livers, and many times the patient is too ill to undergo the surgical operation in the first place.

One suggestion for restoring liver function has been ectopic liver transplantation, where hepatocytes are surgically placed at a site other than the liver of the patient, such as the peritoneum, mesenterium, pancreas, lung parenchyma, fat pads, under the kidney capsule and in the subcutaneous space. Despite these many experimental attempts, all have failed to sufficiently restore liver function because the transplanted cells cannot engraft and/or expand enough to sufficiently compensate for the failing liver. Thus, there is a need for a method of ectopically transplanting liver cells which promotes engraftment and expansion in order to be therapeutically effective.

SUMMARY

Methods of transplanting cells into lymph nodes are disclosed herein. The methods encompass implanting hepatocytes, islet cells, and thymocytes at an ectopic location such as the lymph nodes. Any of a number of lymph nodes can be used including but not limited to the splenic hilar lymph node, celiac lymph node, porta hepatis lymph node, iliac lymph node, paraaortic lymph node, retroperitoneal lymph node, mesenteric lymph node, and abdominal lymph node. Cells can be from any source including allogeneic or syngeneic cells. Concentration ranges include, but are not limited to, $10^4$ to $10^{11}$ cells per lymph node as well as $10^5$ to $10^{10}$ cells per lymph node. Immunosuppressants such as FK506 can be used to overcome any allogeneic graft responses. In certain embodiments, hepatocytes from any source, including stem cells (ES cells and other pluripotent stem cells) and reprogrammed cells (iPS cells) can also be used.

The methods described herein are particularly useful in treating patients with liver disease including rescuing a patient from end-stage liver disease or treating a patient in need of additional hepatic functions. As such, the described methods encompass expanding hepatocytes in a lymph node. It is also contemplated that the method can be used to expand hepatocytes ex vivo wherein donor human hepatocytes are grafted into a non-human recipient lymph node and the hepatocytes are later harvested for implantation into the donor.

BRIEF DESCRIPTION OF THE DRAWINGS

FIGS. 2A-2D are photographs of the anatomic location of enlarged nodules in IP injected mice 10 weeks after transplantation. FIGS. 2A-2B show many enlarged nodules around the stomach region and on the mesenterium observed in a FAH$^{-/-}$ mouse transplanted IP with wild type hepatocytes (circles). Arrow indicates the portal vein. FIG. 2C shows the liver of the IP injected FAH$^{-/-}$ mouse (left) and a control wild type liver (right). The liver of the IP injected FAH$^{-/-}$ mouse was atrophic with a few small regenerative nodules on its surface (arrows). FIG. 2D shows isolated enlarged nodules from same FAH$^{-/-}$ mutant mouse (whose liver appears in FIG. 2C, left panel) with diameters from 1 to 10 mm.

FIG. 4A shows histology and FAH staining of the hepatic lymph nodes from FAH$^{-/-}$ mice transplanted by IP injection of wt hepatocytes. Sections of the enlarged nodules were stained with hematoxylin and eosin (H&E). Serial sections were immunostained with an anti-FAH antibody (brown, HRP staining) then counterstained with eosin. Enlarged nodules are surrounded by a thin capsule, with most of the cells consisting of large polygonal FAH$^+$ hepatocytes. In addition, several islands of small hematopoietic cells were present but no biliary structures were observed. FIG. 4B shows histology (H&E, top row) and FAH staining (bottom row) of native liver from IP injected mouse, which showed that small tumor-like repopulated tissue also consisted of FAH positive hepatocytes. Bar: 100 μm.

FIG. 5A shows CD45, CD3, CD4, and CD8 staining on serial sections. FIG. 5B shows B220, Gr-1, CD11b, and CK18 staining on serial sections. Most of the cells in the enlarged nodule were non-hematopoietic CK18$^+$ hepatocytes, whereas no CK18$^+$ cells could be detected in the normal lymph node. Bar: 100 μm.

As shown in FIG. 7A, these cells were also albumin positive (brown cells, insert in left upper panel) with CK18 and CD26 co-localized (insert in CD26 staining panel). Hepatocyte markers were negative in normal lymph node. In the hepatic lymph nodes, $CD31^+$ endothelial cells corresponding to vessels, similar to those found in normal liver, were observed. In contrast, $CD31^+$ cells indicative of high endothlelial vessels (HEV) found in normal lymph nodes differ in morphology. Bar: 100 μm. FIG. 7B shows immunohistochemistry of engrafted nodule (left panels, A and D), normal liver (center panels, B and E), and normal lymph node (right panels, C anf F) with CD31.

FIG. 9A shows the combined structures of liver hepatic tissue (upper half) and lymph node tissue (lower half) of a lymph node in an IP-injected mouse, where the black line is placed on the border between liver and lymph node structures H: hepatocytes, RBC: red blood cells, L: lymphocytes, SEC: non fenestrated sinusoidal endothelial cells, PC: plasma cells. FIG. 9B shows ultra-structures of normal lymph node. FIG. 9C shows ultrastructure of engrafted hepatic lymph nodes (panels in top row) and control liver (panels in bottom row). In FIG. 9C (left panel, top row), hepatocytes present in hepatic lymph nodes have large prominent nuclei (N), bile canaliculi (BC), mitochondria (M), peroxisomes (P) and rough endoplasmic reticulum (RER). Bar: 2 μm. In FIG. 9C (center panel, top row), higher magnification of the bile canaliculus, containing microvilli (MV) with tight junctions (arrowheads) and adherent junctions (AJ). A lipid vacuole is seen within the canaliculus. Bar: 500 nm. In FIG. 9C (right panel, top row), vessels in hepatic lymph nodes consisted of non-fenestrated sinusoidal endothelial cells (SECs). Bar: 1 μm. FIG. 9C (left panel, bottom row) shows hepatocytes in control liver showing fenestrations (arrows) in SECs. Bar: 2 μm. FIG. 9C (center panel, bottom row) shows higher magnification of bile canaliculus showing tight junctions (arrowheads), lipid vacuoles and Space of Disse (SD). Bar: 500 nm. In FIG. 9C (right panel, bottom row) shows organization of hepatic plates in control livers with bile canaliculi at the apical surface and fenestrated sinusoids (S) at the basolateral surface. Bar: 2 μm.

FIG. 10A is a graph showing the FAH enzyme assay. A standard curve to measure enzyme activity was established using wild type (wt) liver (100% activity), $FAH^{-/-}$ liver (0% activity) and $wt/FAH^{-/-}$ mixes to achieve 15%, 25% and 80% enzyme activity. FAH enzyme activities in engrafted lymph nodes (LN) ranged from 80% to almost 100% of wild-type liver levels. In contrast, FAH enzyme activity in native livers of IP injected mice (diseased liver) had FAH activity ranging from 25% of wild type liver activity to 0% (mean FAH activity of 15% of wild-type liver levels). n=number of mice analyzed. FIGS. 10B-10C shows serial transplantation of lymph node derived hepatocytes. Lymph node derived cells were serially transplanted into $FAH^{-/-}$ mice by splenic (SP) injection. Sections are stained with an anti-FAH antibody that highlight in brown the presence of donor FAH positive hepatocytes. FIG. 10B is a graph showing weight change in IP injected mice was very similar to the change observed in SP injected mice. This demonstrates that lymph node derived hepatocytes can regenerate the liver of $FAH^{-/-}$ mice similar to the regeneration seen by primary hepatocytes. Two selections were necessary due to the low number of hepatocytes transplanted. FIG. 10C is an immunohistology photomicrograph of $FAH^+$ hepatocytes observed in the repopulated liver of $FAH^{-/-}$ mice 8 weeks after transplantation. Bar: 100 μm.

FIGS. 11A-11E and 11G show tissues stained with hematopoietic markers, where FIGS. 11F and 11H show tissues stained with H&E.

FIGS. 12A-12B are immunofluorescence photomicrographs of lymph node from the gastric and common hepatic arteries. FIG. 12A shows photomicrographs of lymph nodes 2 and 3 days after IP injection of wild-type liver cells into $FAH^{-/-}$ mice. On day 2, some $FAH^+CK18^+$ hepatocytes could be detected in lymph nodes. On day 3, clusters of rare $CK18^+$ hepatocytes were seen in lymph nodes primarily composed of $CD45^+$ hematopoietic cells. FIG. 12B shoes photomicrographs of lymph nodes 2 and 3 weeks after IP injection, $FAH^+$ hepatocytes (green) have colonized the lymph nodes and have a high index of proliferation, as demonstrated by the high ratio of BrdU incorporation (red nuclei). 8 weeks after IP injection, few cells are proliferating in lymph nodes. Bar: 100 μm.

FIG. 13A is a photomicrograph of a cluster of $FAH^+$ hepatocytes detected in the lymph node 10 days after transplantation. FIG. 13B is a photograph of a single hepatic lymph node of 1.5×0.5×0.5 cm observed at the injection site 3 months after direct lymph node injection (circle). FIGS. 13C-13D are photomicrographs of H&E-stained single hepatic lymph node 4 weeks after transplantation. Both hepatic and lymphatic tissues coexist in the same nodule. FIG. 13D is a photomicrograph at a higher magnification of the region shown in a black box in FIG. 13C, representing the junction between hepatic and hematopoietic tissues. FIGS. 13E-13F are photomicrographs of single hepatic lymph node 8 weeks after transplantation. Massive hepatic tissue expansion has left only a small remain of lymphatic tissue. FIG. 13F is a photomicrograph at a higher magnification of the region shown in a black box in FIG. 13E, representing the invasion of hepatocytes into the remaining lymphatic tissue. FIGS. 13G-13H are photomicrographs of serial sections with H&E and FAH staining respectively, showing the presence of hepatocytes with remnants of hematopoietic cells in the hepatic lymph node 3 months post injection. Most cells in the hepatic lymph node are FAH+ hepatocytes. Bar: 100 μm.

FIG. 15 shows the immunohistochemistry of liver and transplanted lymph node.

FIG. 17A is a schematic showing an experimental protocol for splenic injection of GFP-C57b1 wild type liver cells into an FAH mutant mouse (129sv), which does not lead to long term survival. FIG. 17B is a graph showing the change in body weight after transplantation. FIG. 17C is a schematic showing an experimental protocol for splenic injection of GFP-C57b1 wild type liver cells into an FAH mutant mouse (129sv) with an immunosuppressive agent (FK506), which may provide for long term survival.

DETAILED DESCRIPTION

Figure 1A:
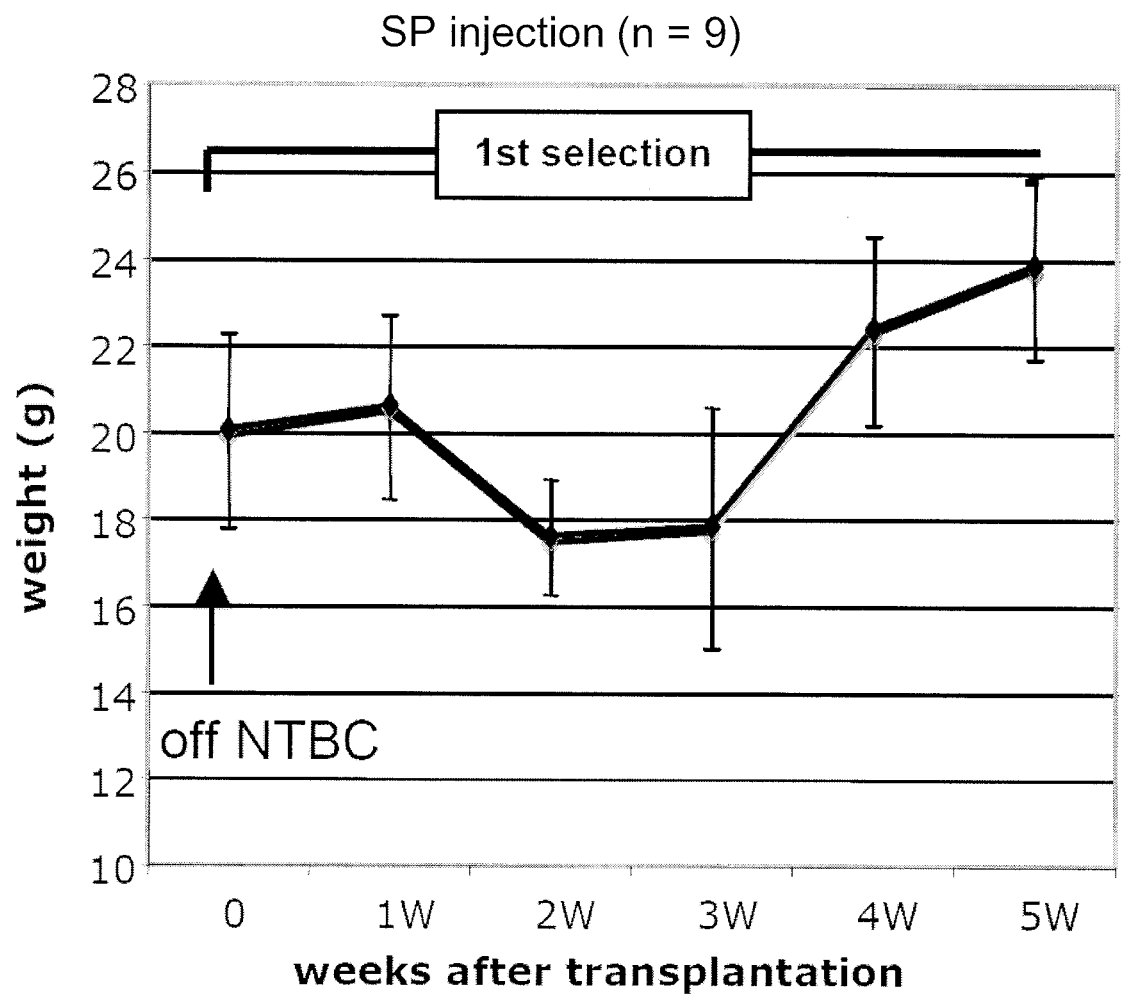
FIGS. 1A-1B are graphs showing the change in body weight of FAH$^{-/-}$ mice after splenic (SP) (FIG. 1A) and intraperitoneal (IP) (FIG. 1B) transplantation, where body weight indicates hepatic regeneration. Body weight of the transplanted mice was monitored weekly after liver cell transplantation, to follow hepatic engraftment and rescue from tyrosinemia. FAH$^{-/-}$ mice transplanted by either SP (FIG. 1A) or IP (FIG. 1B) injections lost weight during the first 3 weeks. Weight loss is indicative of a decline in liver function. SP injected mice (FIG. 1A) spontaneously regained weight (left panel). The IP injected mice (FIG. 1B) had to be rescued by NTBC followed by a second selection prior to regaining weight (right panel), a protocol previously described for engrafting low levels of liver cells (Lagasse, E. et al. Nat Med. 2000; 6:1229-34). All FAH$^{-/-}$ mice that regained weight when taken off NTBC were rescued from tyrosinemia with significant hepatic tissue regeneration. n=number of mice analyzed.

Methods of transplanting hepatocytes, islet cells, and thymocytes at an ectopic location such as the lymph nodes are disclosed herein. Those of ordinary skill in the art recognize that the type of cell implanted, will be depend on the pathology of the patient. For example, hepatocytes can be implanted in patient with hepatic insufficiency; islet cells can be implanted in diabetic patient; and thymocytes can be implanted in patient with immunodeficiencies.

In certain embodiments, hepatocytes can be injected into lymph nodes so that they can expand, thus, supplementing, and, in certain embodiments, replacing liver function for in those of need. In certain embodiments, hepatocytes are allogeneic cells re-programmed from being fibroblasts, stems cell or other cells into hepatocytes. In other embodiments, the hepatocytes are allogeneic hepatocytes transplanted into the patient. Such patients may optionally be placed on immunosupressive therapy to encourage engraftment.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, in reference to elements of an item, composition, apparatus, method, process, system, etc. are meant to indicate that the item, composition, apparatus, method, process, system, etc. includes those elements and that other elements can be included and still fall within the scope/definition of the described item, composition, apparatus, method, process, system, etc. Thus, as a non-limiting example, an apparatus or method that includes elements A, B, C and D may be said to fall within the scope/definition of the apparatus or method said to "comprise" elements A, B and C.

As described herein, hepatocytes or hepatocyte precursors can be implanted into a lymph node or multiple lymph nodes. Such methods are intended to encompass implantation into any lymph node, including, but not limited to: abdominal lymph nodes, celiac lymph nodes, paraaortic lymph nodes, splenic hilar lymph nodes, porta hepatis lymph nodes, gastric lymph nodes (left and right), gastroomental (gastroepiploic) lymph nodes (left and right), retroperitoneal lymph nodes, pyloric lymph nodes (suprapyloric, subpyloric, retropyloric), pancreatic lymph nodes (superior pancreatic, inferior pancreatic, splenic lineal lymph nodes), hepatic lymph nodes (cystic, foraminal—including foramen of Winslow), pancreaticoduodenal lymph nodes (superior pancreaticoduodenal, inferior pancreaticodoudenal), superior mesenteric lymph nodes, ileocolic lymph nodes, prececal lymph nodes, retrocecal lymph nodes, appendicular lymph nodes, mesocolic lymph nodes (paracolic, left colic, middle colic, right colic, inferior mesenteric lymph nodes, sigmoid, superior rectal), common iliac lymph nodes (medial common ilic, intermediate common iliac, lateral common iliac, subaortic common iliac, common iliac nodes of promontory), and external iliac lymph nodes (medial external iliac, intermediate external iliac, lateral external iliac, medial lacunar—femoral, intermediate lacunar—femoral, lateral lacunar—femoral, interiliac external iliac, obturator—external iliac obturatory). In certain embodiments, the cells are injected into a recipient's lymph node from a donor's tissue. In certain embodiments, it is important for the lymph node to be able to swell as the graft expands, and thus lymph nodes that are present in the peritoneal cavity are particularly useful, especially where the lymph nodes are not closely associated with arteries or large veins.

In yet another embodiment, the methods disclosed herein can be useful for treating end-stage liver disease and subsequent liver failure. Liver failure occurs when a large portion of the liver is damaged. Symptoms may include jaundice, tendency to bruise or bleed easily, ascites, impaired brain function, general failing health, fatigue, weakness, nausea, and loss of appetite.

In another embodiment, the methods disclosed herein can be useful for supplementing liver function. As such, the implanted cells serve to augment liver function in a patient with a liver pathology.

In certain other embodiments, hepatocytes transplanted into the lymph node can be given a selective advantage. For example, conditioning protocols for hepatocyte repopulation can be used as described in the art (Gupta, S. et al. Hum Gene Ther. 1994; 5:959-67; Laconi, E. et al. Am J Pathol. 1998; 153:319-29; Guha, C. et al. Cancer Res. 1999; 59:5871-4; Guha, C. et al. Hepatology. 2002; 36:354-62).

Those of skill in the art recognize that transplantation can be made into the lymph node using any cell capable of replacing hepatocytes. As such any cell whether a hepatocyte or a precursor of a hepatocyte can be used for transplantation, as long as liver function is at least partially restored. Thus, in certain embodiments stem cells are transplanted. Lagasse, E., et al., Nat Med, 11:1299-35, 2000. Basma, et al. Gastroenterology; 136:990-999, 2009; Nakagawa, M. et al. Nat Biotechnol.; 26:101-6, 2008; Yamanaka, S. Cell Prolif.; 41 Suppl 1:51-6, 2008. In yet other embodiments, reprogrammed cells are transplanted. A reprogrammed cell is a cell which, although differentiated into a specific cell type, is induced to become another cell type including, for example, metaplastic cells.

Hepatocytes can be prepared by any means known in the art, but in certain embodiments, cell solutions are used for injection. In such embodiments, the cells can be prepared according to the method of Li et al. J Tissue Culture Methods (1992) 14:139-146. Briefly, isolation involves collagenase perfusion of a sample of limited size (<50 g) with only one cut surface. In yet other embodiments, specifically enriched cell populations can be used such as those disclosed in U.S. Pat. No. 7,211,404. Cells can be suspended in any appropriate buffer for injection, including saline, phosphate buffered saline, and Ringer's solution, among others. The injection volume should not rupture the lymph node. Thus, 10 µl, 50 µl, 100 µl, 150 µl, 200 µl, 250 µl, 500 µl or more may be suitable depending on the size of the lymph node.

Engrafted hepatocytes will expand in the lymph node according to the various embodiments presented. Thus, a range of cell concentrations may be used for injections. For example, in some embodiments, $10^4$, $10^5$, $10^6$, $10^7$, $10^8$, $10^9$, $10^{10}$, and $10^{11}$ cells can be injected. Ranges of $10^4$ to $10^{11}$ cells per lymph node as well as $10^5$ to $10^{10}$ cells per lymph are contemplated.

It is also contemplated that the method can be used to expand hepatocytes ex vivo wherein donor human hepatocytes are transplanted into non-human recipient lymph nodes and the hepatocytes are later harvested for implantation back into the donor. In certain other embodiments, human hepatocytes can be implanted in host animals to expand for transplantation back into the human. In such embodiments, any suitable host can be used such as for example a pig. Cells expanded in such a manner can be harvested, purified and injected back into the patient at any site including, for example, the patient's lymph nodes.

In some embodiments, transplant recipients may be additionally administered immunosuppressive agents in order to minimize immune rejection of the grafted hepatocytes. Immunosuppressive agents reduce or prevent an adverse immune response in the recipient mammal to the foreign or grafted tissue by inhibiting or suppressing any innate immune system activity, including, but not limited to, T-cell and/or B-cell activity. Administration of immunosuppressive agents may include, but is not limited to, the administration of radiation therapy and/or the administration of immunosuppressive drugs. Examples of suitable immunosuppressive drugs include, but are not limited to, steroids (such as corticosteroids, dexamethasone, and prednisone), Cox-1 and Cox-2 inhibitors, macrolide antibiotics (such as rapamycin and tacrolimus), and other substances that limit, reduce, or suppress B-cell, T-cell, and/or other innate immune activity. Immunosuppressive agents particularly suitable for use with the present invention include those immunosuppressive agents known for use with liver transplantation, including, but not limited to, steroids, cyclosporine, rapamycin, azathioprine, prednisone, and OKT3. In a preferred embodiment, hepatocyte graft recipients are administered the immunosuppressive agent tacrolimus, also called FK506, a calcineurin inhibitor that in turn inhibits IL-2 production and downstream B-lymphocyte activation.

EXAMPLES

Described below are materials and methods used throughout the following examples, unless otherwise specified.

Animals: $FAH^{-/-}$ mice kindly were used for recipients and 129S4 congenic mice were used for donors. Freshly isolated hepatocytes were obtained from 8- to 12-week-old 129S4 mice and were transplanted into 8- to 12-week-old $FAH^{-/-}$ mice according to institutional guidelines.

Antibodies: The antibodies used in the immunohistochemistry were as followed. The primary antibodies used were rat anti-mouse CD31, rat anti-mouse CD45, rat anti-mouse CD45/B220, rat anti-mouse Gr-1, rat anti-mouse CD90.2, hamster anti-mouse CD3, mouse anti-mouse CK18, rabbit anti-mouse VCAM1, goat anti-mouse CK19, rat anti-mouse F4/80 and rat anti-mouse E-cadherin. The primary antibodies used were phycoerythrin (PE)-conjugated rat anti-mouse CD31, CD45, CD45/B220, Gr-1, CD3, CD4, CD8 and CD11b, FITC conjugated rat anti-mouse CD26, mouse anti-mouse CK18, rat anti-mouse CD62L, purified goat anti-mouse albumin, goat anti-mouse CK19, goat anti-Desmin, anti-mouse BrdU, rabbit anti-GFAP, rat anti-mouse F4/80, rat anti-mouse E-Cadherin, anti-mouse CCR7 and anti-mouse CXCR4.

The secondary antibodies used were fluorescein isothiocyanate (FITC)-conjugated chicken anti-rat immunoglobulin G (IgG), phycoerythirin (PE)-conjugated chicken anti-rat IgG, goat anti-rabbit IgG 594, chicken anti-goat IgG 594, biotinylated anti-rat and mouse anti-hamster IgG and streptavidin-PE. All of the antibodies were diluted to the optimal concentration with phosphate buffer saline (PBS).

Cell preparation: Hepatocytes were harvested using the 2-step collagenase perfusion technique as described by Seglen, J Toxicol Environ Health 1979; 5(2-3): 551-60 incorporated by reference in its entirety. Briefly, 8 to 12 week old 129S4 mice were anesthetized by intraperitoneal injection of Avertin (2-2-2 Tribromoethanol). The laparotomy was performed to expose the inferior vena cava (IVC). A 20G IV catheter was inserted into inferior vena cava. The liver was perfused with calcium- and magnesium-free Earle's balanced salt solution (EBSS) supplemented with 0.5 mM EGTA and 10 mM HEPES for 5 minutes and then calcium- and magnesium-plus Hank's buffered salt solution (HBSS) for 5 minutes. The solution was changed to EBSS supplemented with 0.1 mg/ml collagenase type II (GIBCO, CA) for 30 minutes. The liver was minced in cold HBSS and filtered through a 70 µm nylon mesh. Low centrifuge at 50 g for 2 minutes was performed three times to purify hepatocytes. The number and viability of cells were determined by trypan blue exclusion. One million viable cells were suspended in 30 µl HBSS and kept on ice until the time of transplantation.

Transplantation: For intraperitoneal hepatocyte transplantation, one million viable hepatocytes were injected into the lower peritoneal cavity through 28-gauge needle. For splenic hepatocyte transplantation, animals were anesthetized and a small surgical incision was made in the left flank. The spleen was exposed and $0.2 \times 10^6$ hepatocytes, suspended in 30 µl HBSS, were injected into the inferior pole of the spleen using a 28-gauge needle. The injection site was ligated to prevent cell leakage and bleeding. All mutant mice were kept on 2-(2-nitro-4-trifluoro-methylbenzyol)-1,3-cyclohexanedione (NTBC) until the time of transplantation. NTBC was discontinued just after transplantation. The weight of experimental animals was measured weekly.

FAH staining: Harvested tissues fixed in 10% phosphate-buffered formalin, pH 7.4, were dehydrated in 100% ethanol and embedded in paraffin wax at 58° C. Five μm sections were de-paraffinized, and stained with hematoxylin-eosin and with a polyclonal rabbit antibody to FAH. The antibody was diluted in phosphate buffered saline pH 7.4 and applied at concentrations of 1:25 at 37° C. for 1 hr. Endogenous peroxidase activity was blocked with 3% $H_2O_2$ and methanol for 15 min. Nonspecific binding was blocked with 0.5% skim milk for 30 min SUPERSENSITIVE™ Multilink and then Peroxidase Conjugated Strepavidin were used as the secondary and tertiary antibody respectively. Color development was performed with the AEC detection kit.

Immunohistochemistry: Harvested tissues were embedded in optimum cutting temperature compound and frozen in isopentane. Serial sections 5 μtm in thickness were fixed in acetone for 10 minutes at −20° C. Then, nonspecific binding was blocked with 2% bovine serum albumin for 45 minutes. Subsequently, they were incubated with the primary antibody for 2 hours at room temperature followed by incubation with fluorescence conjugated secondary antibody for 45 minutes at room temperature. Nuclear counterstain was done with 4',6-diamidino-2-phenylindole. The signal was detected using a fluorescent microscope. For 5-bromodeoxyuridine (BrdU) staining, BrdU (30 mg/kg) was administered intraperitoneally 4 hours prior to sacrifice. The fixed serial sections were incubated with 2N HCl for 20 minutes at room temperature, followed by the some protocol as above.

Biochemical analysis: Animals were anesthetized using AVERTIN® and the laparotomy was performed to expose IVC. Blood was collected from IVC and immediately mixed with 10 μl of Na-heparin for anticoagulation. Red blood cells were removed by a brief centrifugation and the plasma was frozen at −80° C. AST, ALT, creatinine, total/direct bilirubin, and amino acids analysis were performed.

FAH enzyme assay: FAH enzyme assays were carried out at 37° C. as described by Know et al., Meth Enzym 1955; 2: 287-300, incorporated by reference in its entirety. The harvested tissues stored at −80° C. was homogenized and sonicated in complete lysis M buffer. Protein concentrations were measured with BCA® protein assay kit (Pierce, Rockford, Ill.) and adjusted at 3 μg/ml. 8 μl of fumarylacetoacetate (FAA), the substrate for the FAH assay, was incubated with each protein solution, and the disappearance of absorbance at 330 nm was measured spectroscopically every 10 seconds. Wild-type and FAH$^{-/-}$ livers were used as positive and negative controls. FAA was prepared enzymatically from homogentisic acid according to Knox W E, J Biol Chem 1955; 216(2): 479-87.

Re-transplantation of the cells from small nodules: Harvested small nodules were minced into small pieces and incubated in 0.1 mg/ml collagenase type II solution supplemented with 0.05 mg/ml DNase I (Sigma) at 37° C. for 30 minutes. The isolated cells were collected by filtration through a 70 μm nylon mesh and washed three times with HBSS. The number and viability of cells were determined by trypan blue exclusion. About $10^5$ to $2\times10^5$ cells were suspended in 30 μl HBSS and transplanted by splenic injection as described above.

Transmission electron microscope: Harvested tissues were fixed with 2% paraformaldehyde and 0.01% gluteraldehyde in 0.1M PBS and were stored at 4° C. for 1 h. Pieces of the fixed tissue were infused with 2.3M sucrose in 0.1M PBS overnight at 4° C. Tissue was frozen on ultracryotome stubs under liquid nitrogen and was stored in liquid nitrogen until use. Ultrathin sections (70-100 nm) were cut using a Reichert Ultracut U™ microtome with a FC4S cryoattachment, lifted on a small drop of 2.3M sucrose, and mounted on Formvar-coated copper grids. Sections were stained in 2% neutral uranyl acetate for 7 minutes, washed three times in sterile water, stained for 2 minutes in 4% uranyl acetate, and then embedded in 1.25% methyl cellulose. The sections were examined by transmission electron microscopy.

Reverse-Transcription Polymerase Chain Reaction (RT-PCR): Total RNA was extracted from the harvested tissues using an RNEASY™ kit (QIAGEN, Chatsworth, Calif.) according to the manufacturer's instructions. Complementary DNA was synthesized from total RNA using the OMNISCRIPT™ RT kit (QIAGEN) and amplified using specific primer pairs and AMPLITAQ GOLD™ DNA polymerase (Perkin Elmer, Foster City, Calif.). The PCR conditions were as follows: 96° C. for 5 minutes, followed by 36 cycles of 96° C. for 30 seconds, 56° C. (54° C. for SIP1, albumin for 58° C.) for 1 minute and 72° C. for 1 minute, and a final extension at 72° C. for 10 minutes. The primers used were as follows:

```
                                          (SEQ ID NO: 1)
5'-GGAAGCCCAACTATAGCGAGC-3' (mouse Snail forward), (SEQ ID NO: 2)
5'-CAGTTGAAGATCTTCCGCGAC-3' (mouse Snail reverse), (SEQ ID NO: 3)
5'-GCACTGTGATGCCCAGTCTA-3' (mouse Slug forward), (SEQ ID NO: 4)
5'-AGCAGCCAGACTCCTCATGT-3' (mouse Slug reverse), (SEQ ID NO: 5)
5'-GTCCATGCGAACTGCCATCTGATCCGCTCT-3'
(mouse SIP1 forward), (SEQ ID NO: 6)
5'-GGCTTGCAGAATCTCGCCAC-3' (mouse SIP1 reverse), (SEQ ID NO: 7)
5'-CGAGAAGCTTGGAGAATAT (mouse albumin forward), (SEQ ID NO: 8)
5'-GTCAGAGCAGAGAAGCAT-3' (mouse albumin reverse), (SEQ ID NO: 9)
5'-TGGAGAAGAGCTATGAGCTGC (mouse β-actin forward),
and (SEQ ID NO: 10)
5'-GATCCACATCTGCTGGAAGG (mouse β-actin reverse).
```

Example 1

Rescue of Lethal Hepatic Failure by Functional Ectopic Liver in Lymph Nodes

To explore the feasibility of creating a functional ectopic liver, a mouse model of hereditary tyrosinaemia type I (HT I) was used as described by Grompe, M. et al. Nat Genet. 1995; 10:453-60 and Overturf, K., et al. Am J Pathol 1997; 151: 1273-80, both of which are incorporated by reference in their entirety. Specifically, HT I is a liver disease caused by deficiency of the enzyme fumarylacetoacetate hydrolase (FAH). Knockout mice (FAH$^{-/-}$ tyrosinemic mice) have progressive and fatal liver failure. FAH catalyses the breakdown of fumarylacetoacetate (FAA), a reactive and toxic compound that is the last step in tyrosine degradation. The accumulation of FAA causes progressive liver failure and animals eventually die. However, the accumulation of FAA can be prevented by administration of 2-(2-nitro-4-trifluoromethylbenzoyl)-1, 3 cyclohexane dione (NTBC). NTBC (also known as nitisone and ORPHADIN®) is a specific inhibitor of an enzyme directly upstream of FAH that catalyzes the production of FAA. Thus, induction of liver failure can be controlled by removing animals from NTBC treatment.

Wild type hepatocytes have a strong selective growth advantage when transplanted in the liver of FAH$^{-/-}$ mice after NTBC removal, with near-complete regeneration of the liver (Overturf, K., et al. Am J Pathol. 1997; 151:1273-80; Lagasse, E., et al. Nat Med. 2000; 6:1229-34, both of which are incorporated by reference in their entirety). To evaluate possible ectopic locations for transplant, liver cells from congenic wild type mice were transplanted in FAH$^{-/-}$ tyrosinemic mice under the skin (n=5), under the kidney capsule (n=5) or intraperitoneally (IP) (n=50), with splenic injection (SP) used as a positive control (n=21). NTBC was removed to induce progressive liver failure in all the transplanted animals, and their weight was monitored weekly as an indicator of liver function.

The overall survival rate of SP injected mice and IP injected mice were 90.4% (19/21) and 80.0% (28/35) respectively. The weights of transplanted animals were usually followed weekly. It is reported that all non-transplanted mutant animals first began losing weight 1 week after stopping NTBC and then died within 2 months.

SP mice initially lost weight until 4 to 5 weeks after transplantation and then spontaneously regained weight (FIG. 1A) with donor hepatocytes repopulating the entire diseased liver and reversing lethal tyrosinemia (19/21 mice transplanted, 90.4% survival). During the weight loss, the transplanted cells maintained a strong selective advantage and proliferated in FAH$^{-/-}$ mice livers until the transplanted hepatocytes repopulated entirely. Subcutaneous injections and injections under the kidney capsule failed to rescue FAH$^{-/-}$ mice. However, IP transplantation of liver cells resulted in long-term survival of these animals (FIG. 1B) after two periods of selection via removal of NTBC (42/50, 84% survival).

Figure 1B:
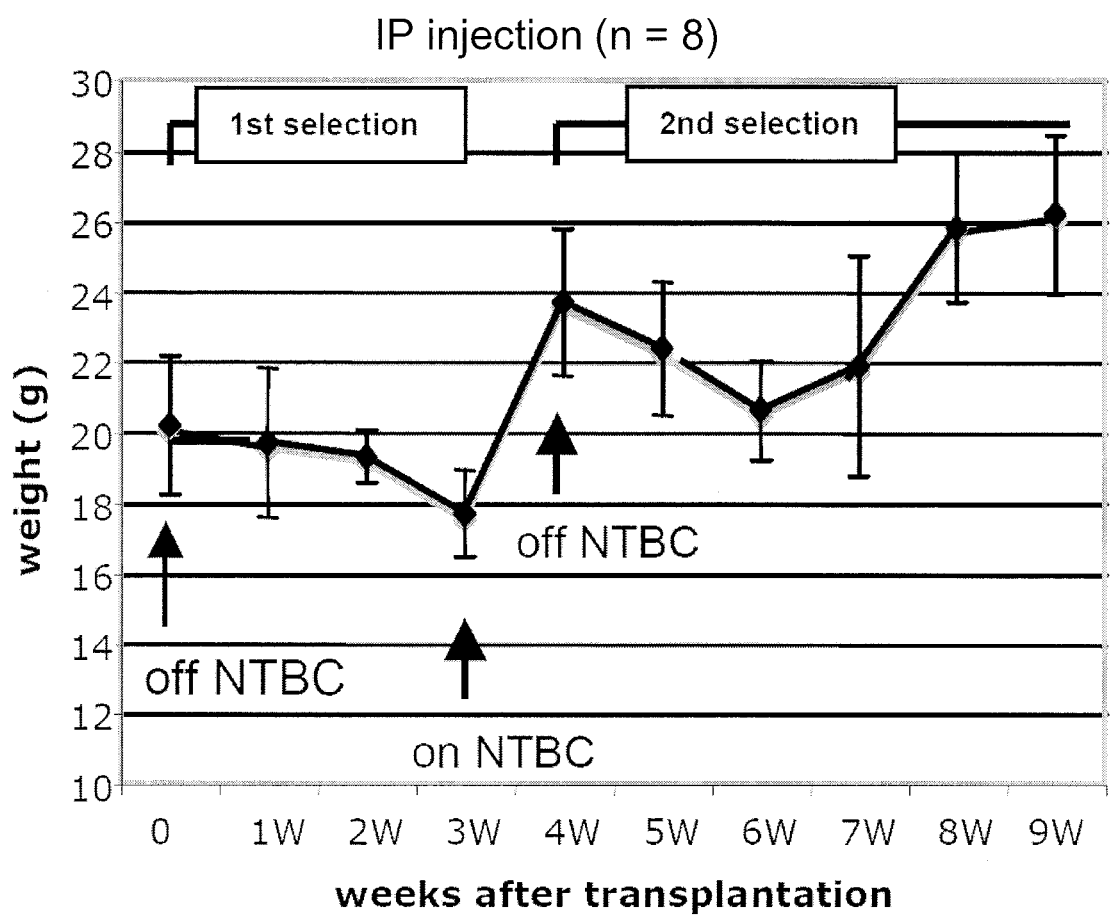

The IP injected mice lost weight as well after transplantation, but did not spontaneously gain weight and thus needed to be put NTBC again. Under the second selection, they lost weight again and then spontaneously started to gain weight (FIG. 1B). This indicated that IP injected cells could not engraft fully enough to recover from liver dysfunction under the first selection; however eventually the transplanted cells engrafted and became functional.

Figure 11:
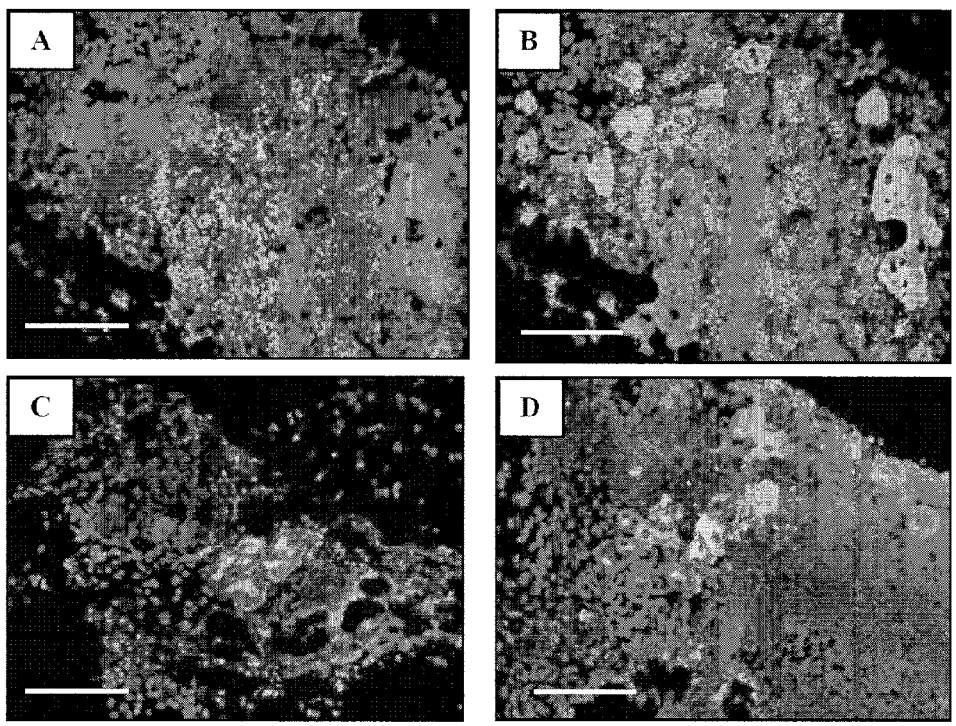
FIG. 11 are immunofluorescence and immunohistochemical photomicrographs of lymph node on Day 2 (FIGS. 11A-11D, Fah staining in red and ck18 in green) and Day 3 (FIGS. 11E-11H, CK18 in green and CD45 in red) after IP injection.
Figure 11:
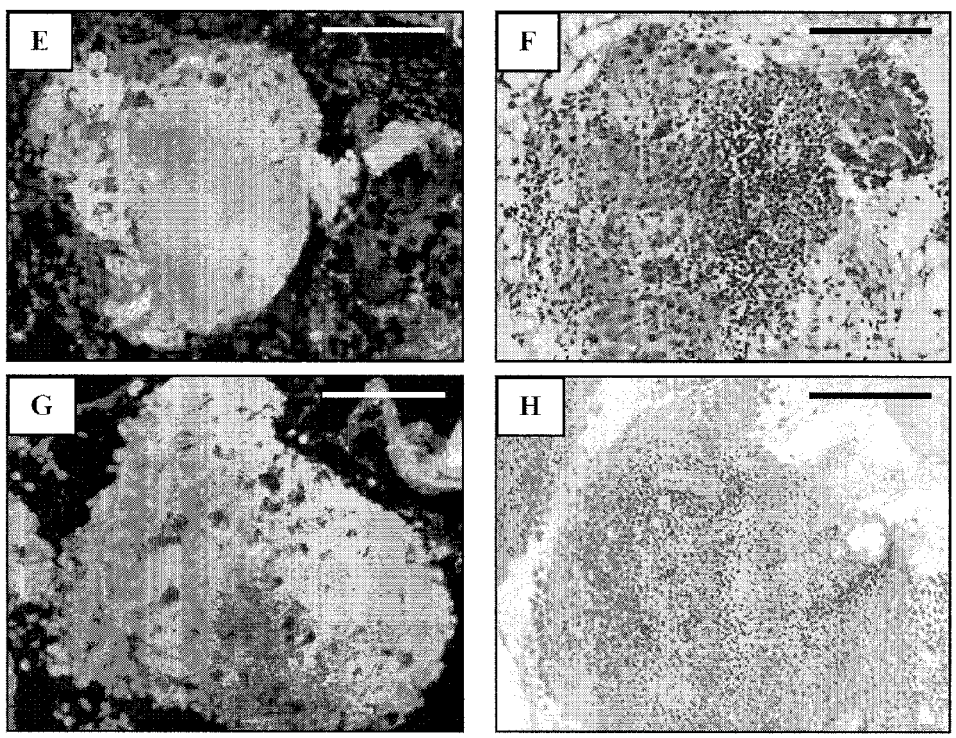

In the IP injected FAH$^{-/-}$ mice, it was observed that donor hepatocytes rapidly colonized the lymphatic system instead of the liver. Within two days after IP transplantation, hepatocytes were detected adjacent to the lymphoid cells in the subcapsular sinus of lymph nodes located along the gastric and common hepatic arteries (FIG. 11 and FIG. 12A). Two weeks after transplantation, hepatocytes had entirely colonized the lymph nodes (FIG. 12B). This outcome suggests that hepatocytes can rapidly migrate into the lymphatic system through afferent lymph vessels, proliferate, and then passively or actively eliminate lymphocytes from the lymph nodes.

Figure 2D:
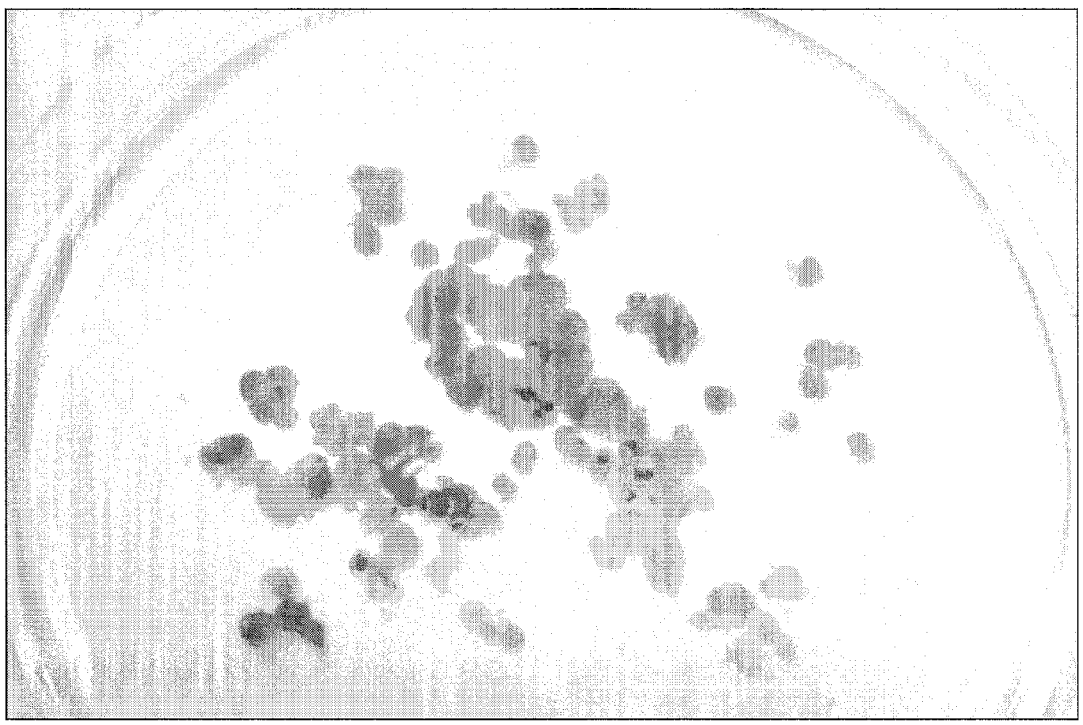

Macroscopic findings of IP injected mice. To determine where the transplanted cells engrafted, laparotomy was performed. Ten weeks post transplantation, after apparent reversal of tyrosinemia, laparotomies were performed on the experimental mice. Numerous small red liver-like enlarged nodules, which had diameters from 1 to 10 mm (FIG. 2D), were generated around stomach and on the mesenterium (FIGS. 2A and 2B). None of these enlarged nodules were found in SP transplanted FAH$^{-/-}$ mice. The distribution of nodules matched the expected distribution of lymph nodes present in these regions. According to further observation, these nodules mainly distributed along the gastric, gastroepiploic, splenic, and hepatic artery as well as the portal vein. This distribution of nodules was very similar to that of the lymphatic system around stomach.

Figure 3:
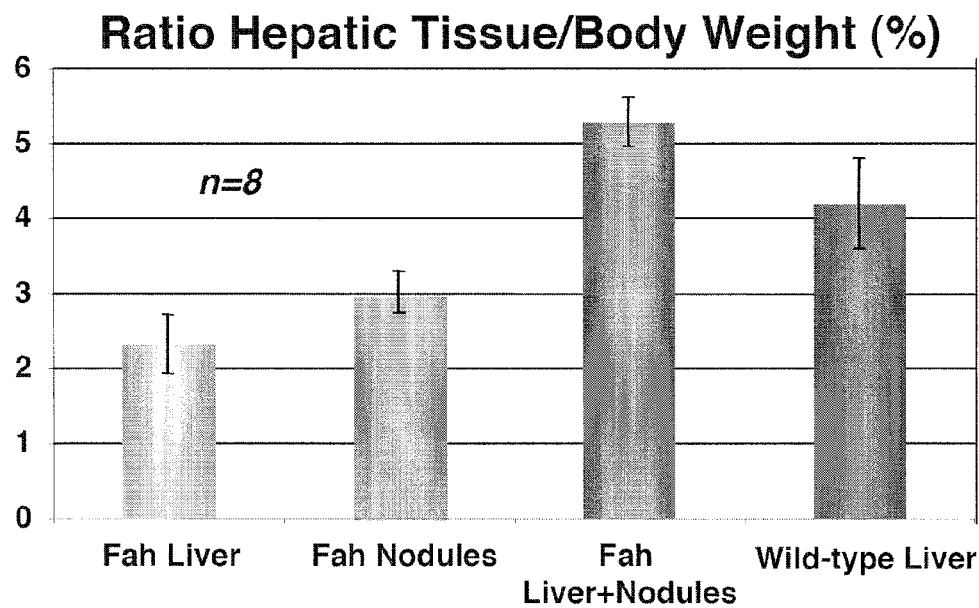
FIG. 3 is a graph of the ratio±s.d. of the weight of liver+enlarged nodules to body weight. The ratio of hepatic tissues to body weight was determined in FAH$^{-/-}$ mice that underwent IP transplantation. FAH$^{-/-}$ mice were killed 10 weeks after liver cell transplantation and both liver (atrophic) and enlarged nodules (hypertrophic) were collected and compared to normal wild-type (wt) liver. n=number of mice analyzed.

On the other hand, the native livers from IP injected mice were atrophic and some small tumor-like repopulating tissue could be observed on the surface (FIG. 2C). To determine the ratio of tissues against body weight, the weight of animals and the tissues were measured. The ratios of normal wild-type liver, the native liver from IP injected mice and the nodules were 4.19±0.60%, 2.32±0.39% and 3.00±0.28% respectively. Additionally, the ratio of total weight of native liver and nodules from IP injected mice was 5.28±0.33% (FIG. 3).

FAH Staining and Immunohistochemistry.

Immunohistological analysis confirmed the presence of donor hepatocytes in all the analyzed enlarged nodules. The newly generated "hepatic lymph nodes" had a mass of ectopic liver cells representing over 70% of expected normal liver mass (FIG. 3) with the number of hepatocytes estimated at $1.5 \times 10^7$ of the $2 \times 10^7$ liver cells. This massive ectopic generation of liver tissue subsequently rescued the animal from lethal liver failure.

Figure 4A:
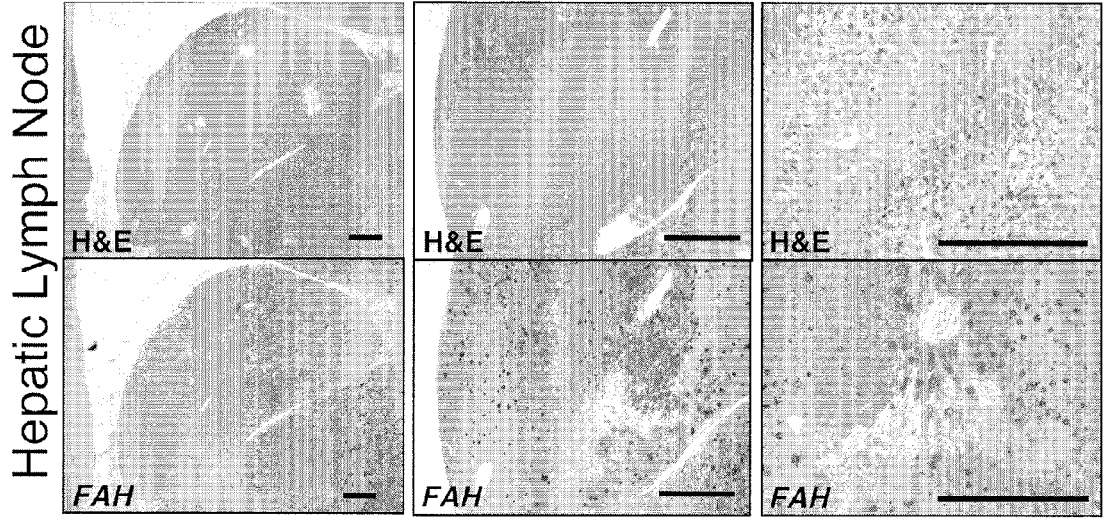
FIGS. 4A-4B are immunohistology photomicrographs of H&E and FAH-stained hepatic lymph nodes at 10 weeks after transplantation and of the liver from IP-injected mouse.
Figure 4B:
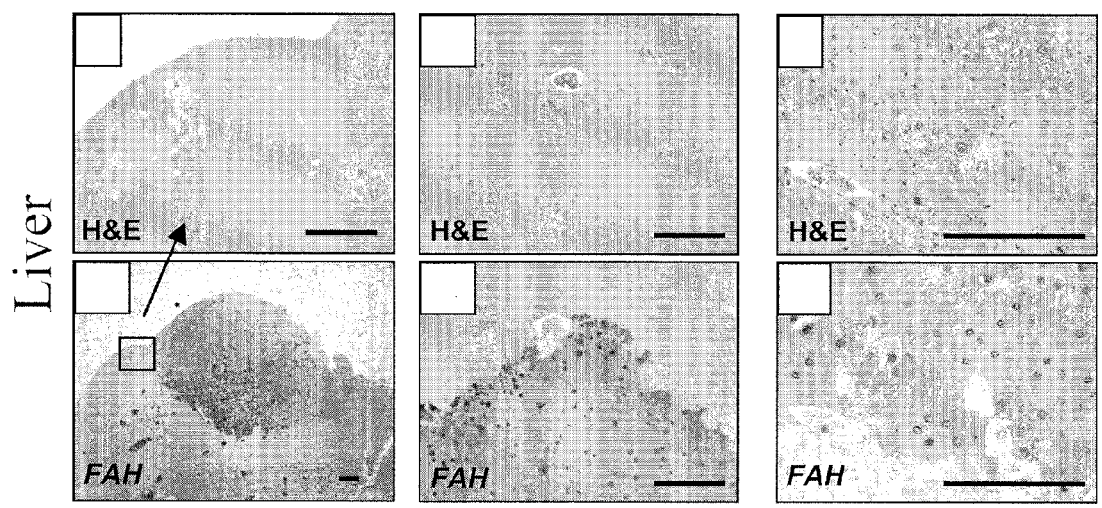

To examine the structure of nodules, H&E staining was performed (FIG. 4A). H&E staining of nodules showed that nodules were surrounded by a thin capsule, and most of cells consistied of nodules that were large and polygonal, which were morphologically similar to hepatocytes (FIG. 4A, top row). Other than these cells, several islands of small cells and vessel-like ductal structures could be observed (FIG. 4A, right panel, top row). To characterize these large and polygonal cells, FAH staining was performed. Most of these large and polygonal cells were FAH positive (FIG. 4A, bottom row) and this result indicated that transplanted FAH positive hepatocytes engrafted in these nodules. In contrast, FAH staining of the native liver from IP injected mouse showed that small tumor-like repopulated tissue also consisted of FAH positive hepatocytes (FIG. 4B, bottom row). H&E staining of native liver showed that lobular structure and cord-sinusoid pattern were mildly distorted and some ballooned hepatocytes could be detected.

Figures 5A, 5B:
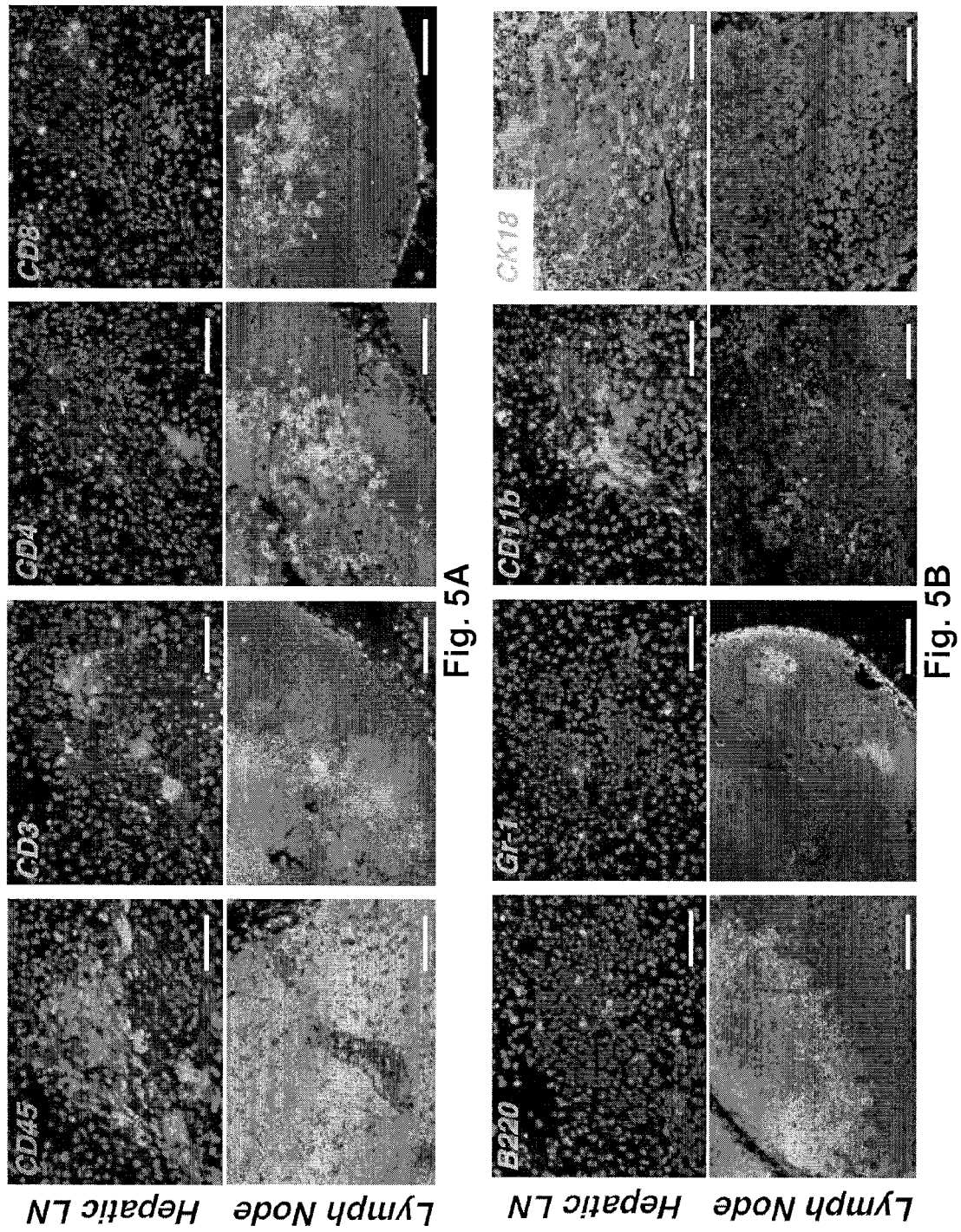
FIGS. 5A-5B are immunofluorescence photomicrographs of the hepatic lymph nodes (Hepatic LN) and normal lymph nodes (Lymph Node) with hematopoietic markers 10 weeks after IP injection of wild-type liver cells in FAH$^{-/-}$ mice. Each staining has two panels, the top panel represents the enlarged nodules engrafted with hepatocytes (hepatic LN) in FAH$^{-/-}$ mice and bottom panel is normal wild type mouse lymph node (Lymph Node).
Figure 6:
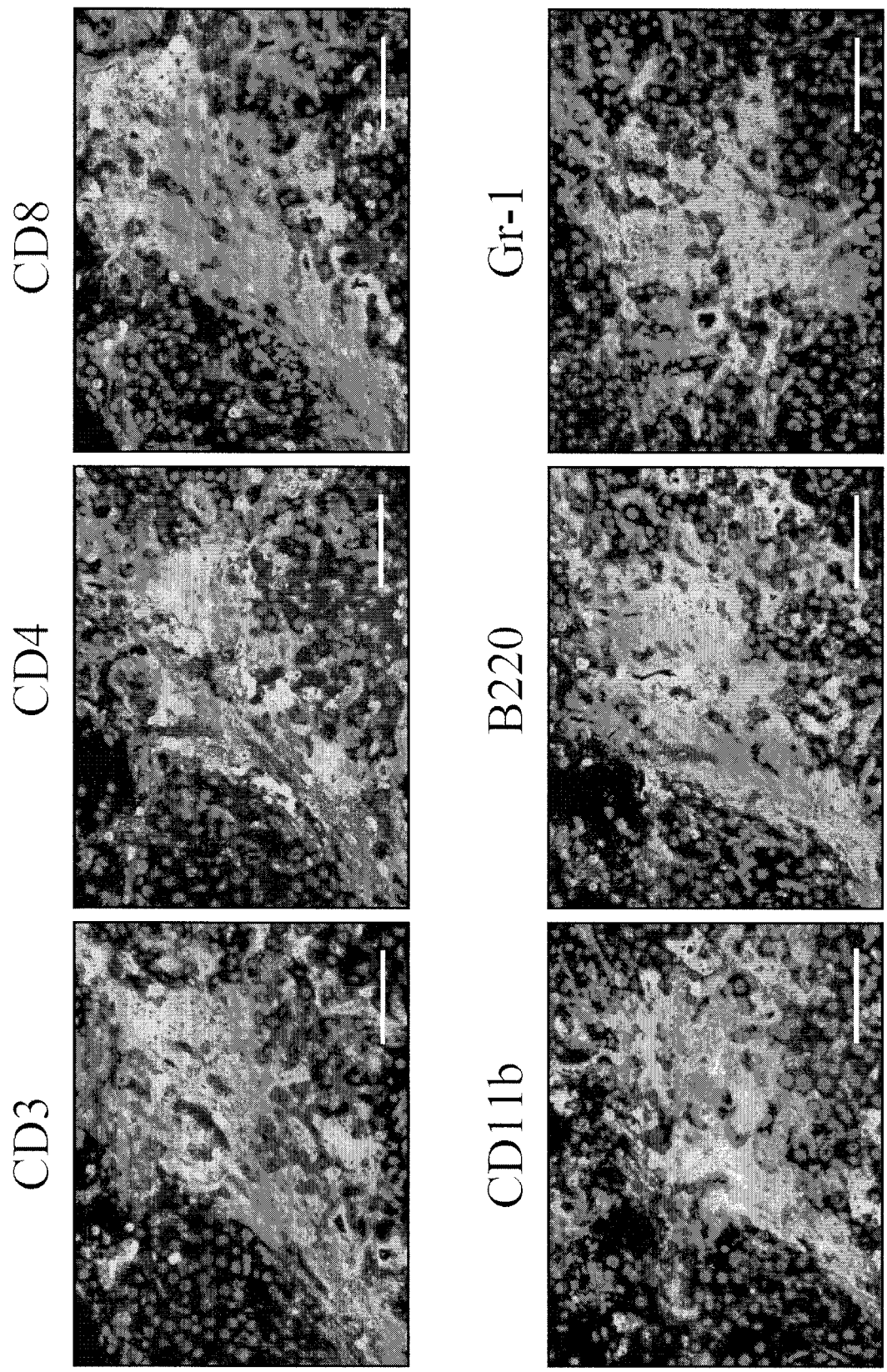
FIG. 6 are immunofluorescence photomicrographs for CD45 (green) and hematopoietic markers (red, including CD3, CD4, CD8, CD11b, B220, and Gr-1) in engrafted lymph nodes. Bar: 100 μm.
Figure 7A:
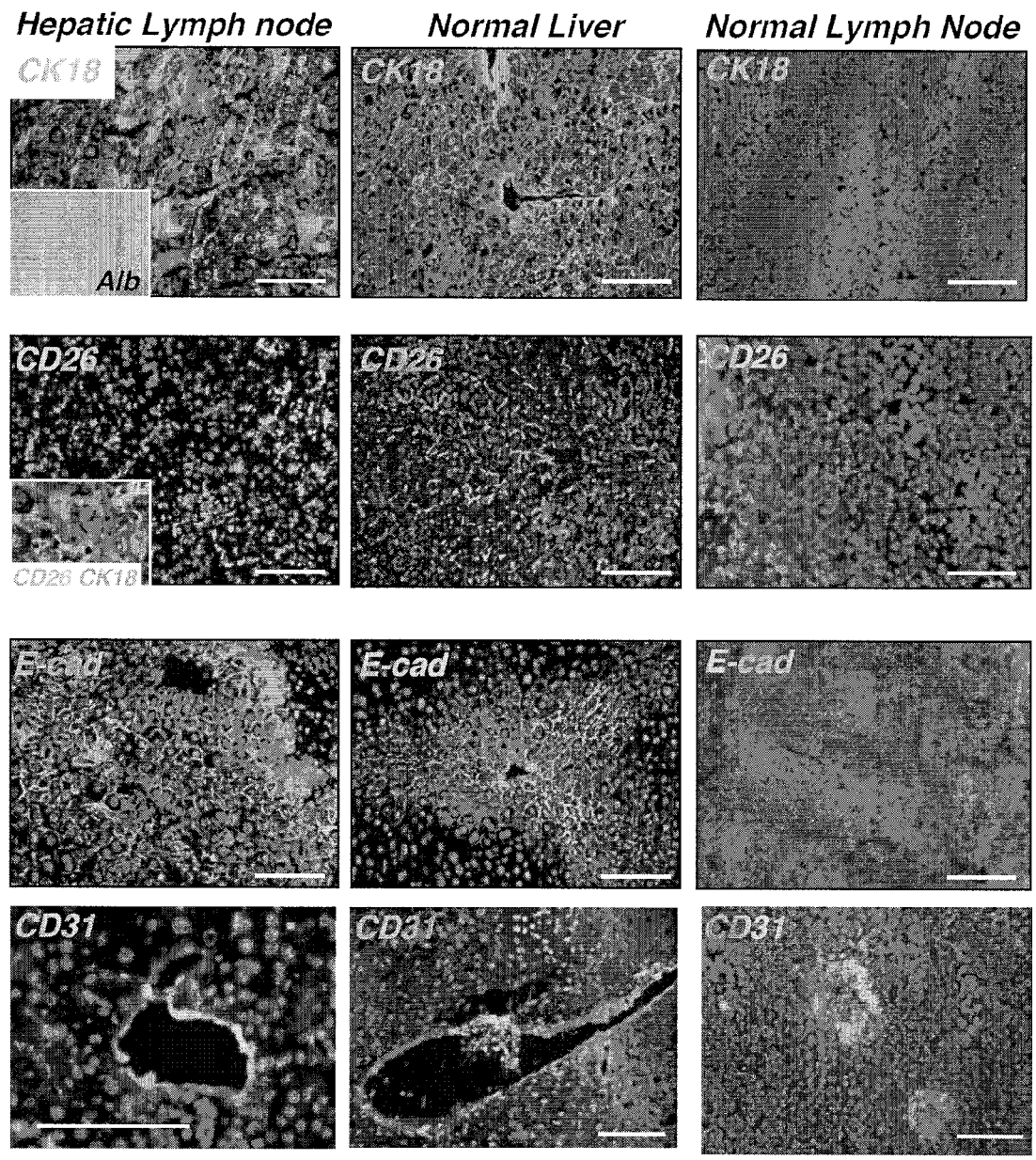
FIGS. 7A-7B are immunofluorescence photomicrographs of the hepatic lymph nodes, normal liver and normal lymph nodes with hepatocyte markers CK18, CD26, E-Cadherin and the endothelial marker CD31. Most of cells in the enlarged nodules were positive for hepatocyte markers, with expression patterns similar to those of the normal control liver.
Figure 7B:
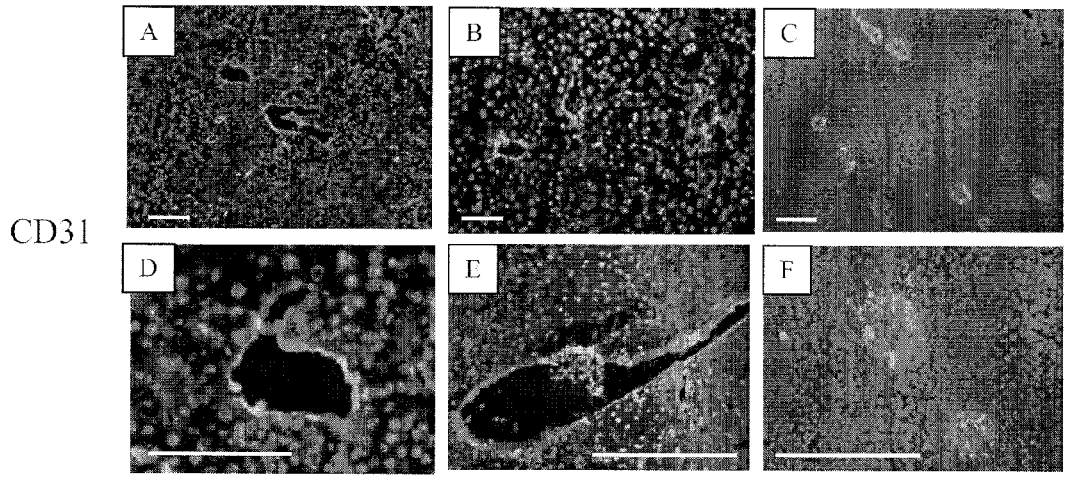

To characterize islands of small cells and ductal structure, immunohistochemistry was performed (FIGS. 5-7). Most of small cells expressed CD45 (FIGS. 5 and 6), which is a marker of hematopoietic cells, and a small population of these CD45 positive cells expressed CD45/B220 (FIG. 5), which is a marker of B cells. However, they did not express CD3, Thy1.2, which is a marker of T cells, and Gr-1, which is a marker of granulocytes. On the other hand, vessel-like ductal structures were CD31 (FIGS. 7A-7B) and VCAM1 positive which are a marker of endothelial cells. The structure of these CD31 positive vessels was completely different from the CD31 positive blood vessels in normal lymph nodes (FIG. 7A). CK19 positive cells, which are thought to be biliary epithelial cells, could not be clearly detected. Additionally, most of cells engrafted in nodules were positive for CK18 (FIG. 7A), which is a marker of hepatocytes. Interestingly, F4/80 positive cells, which are thought to be specific for macrophage/Kupffer cells, distributed between CK18 positive cells (FIG. 8) and this distribution is very similar to the one in normal liver. These results showed that the intraperitoneally transplanted hepatocytes engrafted in these nodules and developed liver-like structure except for a biliary system.

Figure 8:
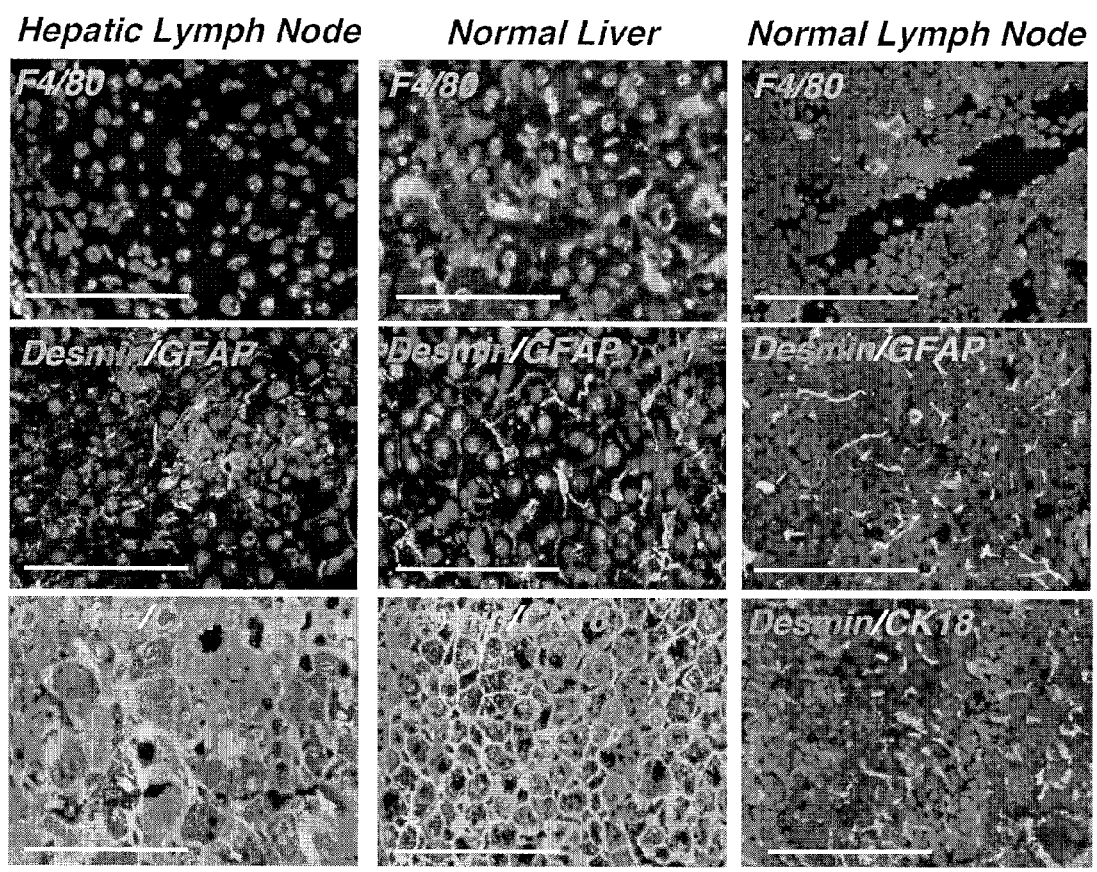
FIG. 8 are immunofluorescence photomicrographs of the hepatic lymph nodes (10 weeks after IP injection of wild-type liver cells into $FAH^{-/-}$ mice), normal (wild type) liver and normal (wild type) lymph nodes with the hepatocyte marker, CK18 and the non-parenchymal cell markers F4/80, Desmin, and GFAP. $F4/80^+$ Kupffer cells were widely distributed in normal liver but only a few $F4/80^+$ macrophages could be detected in normal lymph node. No confirmed $F4/80^+$ cells could be observed in the hepatic lymph nodes. Desmin and GFAP, two markers of stellate cells in the liver, were widely distributed in the hepatic lymph nodes, normal liver and normal lymph nodes. The $Desmin^+$ cells were distributed between $CK18^+$ hepatocytes in hepatic nodule and normal liver, but Desmin and $GFAP^+$ positive cells were also detected in normal lymph node. Bar: 100 μm.
Figure 9A:
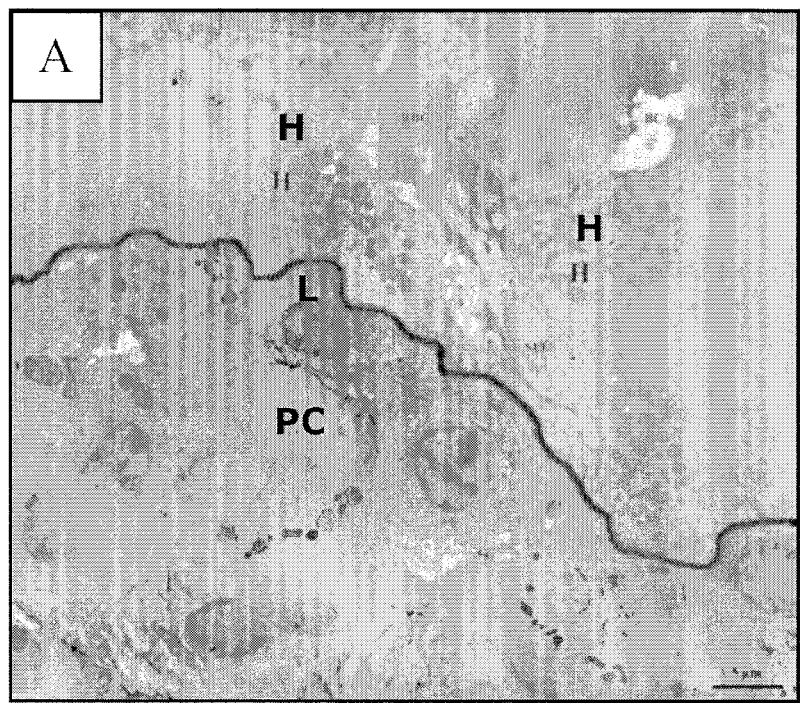
FIGS. 9A-C are transmission electron micrographs of hepatic lymph nodes and of wild-type liver.
Figure 9B:
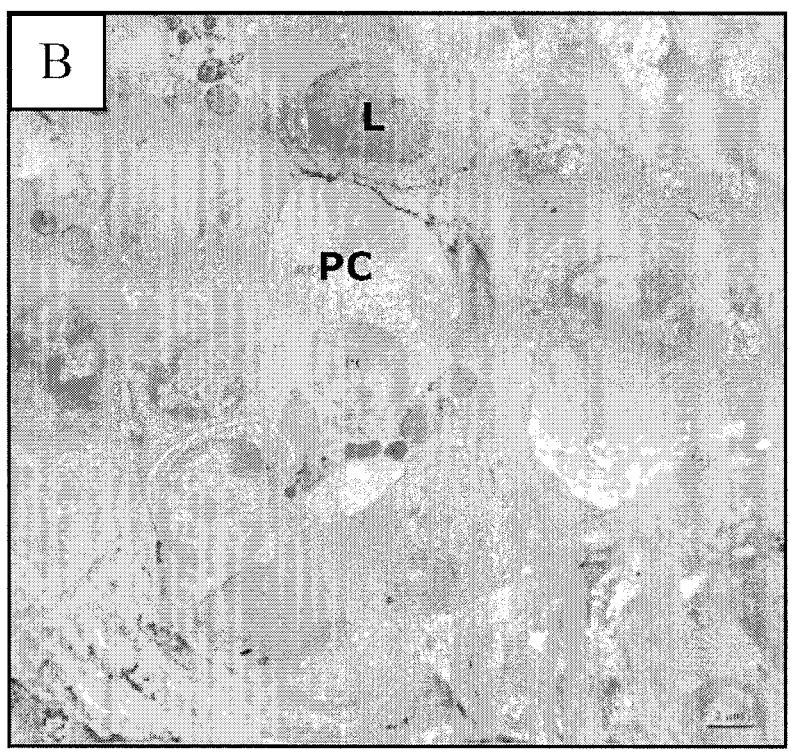
Figure 9C:
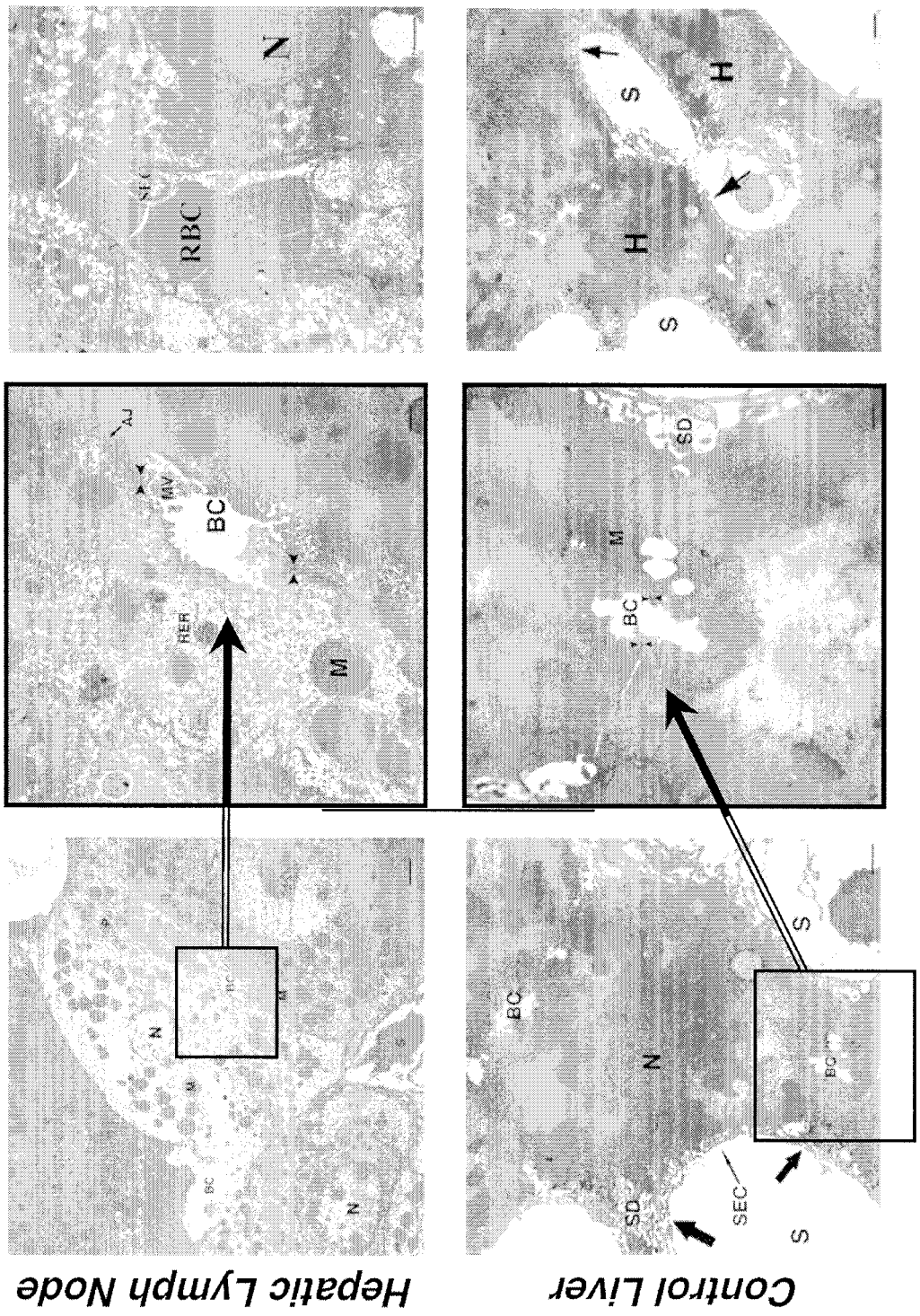

Further analysis of the hepatic lymph nodes showed that not only had the lymphocytes almost completely disappeared (FIG. 5), but High Endothelial Venules (HEVs), the specialized postcapillary venules found in lymphoid tissue were also absent in lymph nodes after hepatocyte colonization (FIG. 7A). The HEVs were replaced by vessels with histology similar to that found in normal liver, but lacking characteristic fenestrations (FIG. 9C). Hepatic lymph nodes were negative for CK19, a biliary epithelial marker, and F4/80, a macrophage/Kupffer cell marker (FIG. 8). Expression of the stellate cell markers, Desmin and GFAP, was detected. However, because these markers were also present in normal lymph nodes, identification of hepatic stellate cells was inconclusive (FIG. 8).

Immunohistochemistry was performed on the lymph nodes on Day 2 (FIGS. 11A-D, where 11A and 11B are the same section) and Day 3 (FIGS. 11E-H, where 11F and 11H are H&E staining of 11E and 11G) after IP injection of wild-type liver cells in FAH mutant mouse. On Day 2, some FAH (FIG. 11A, red) and CK18 double positive hepatocytes (FIG. 11B, green) could be detected in lymph nodes. These CK18 positive hepatocytes (red) also expressed CD26 (green) and double positive cells could be detected (FIGS. 11C, D as yellow cells). On Day 3, cluster of CK18 positive (green) hepatocytes migrated into the lymph node consisting of CD45 positive (red) hematopoietic cells (FIGS. 11E, G) and these larger cells could be observed by H&E staining (FIGS. 11F, H).

Figure 14:
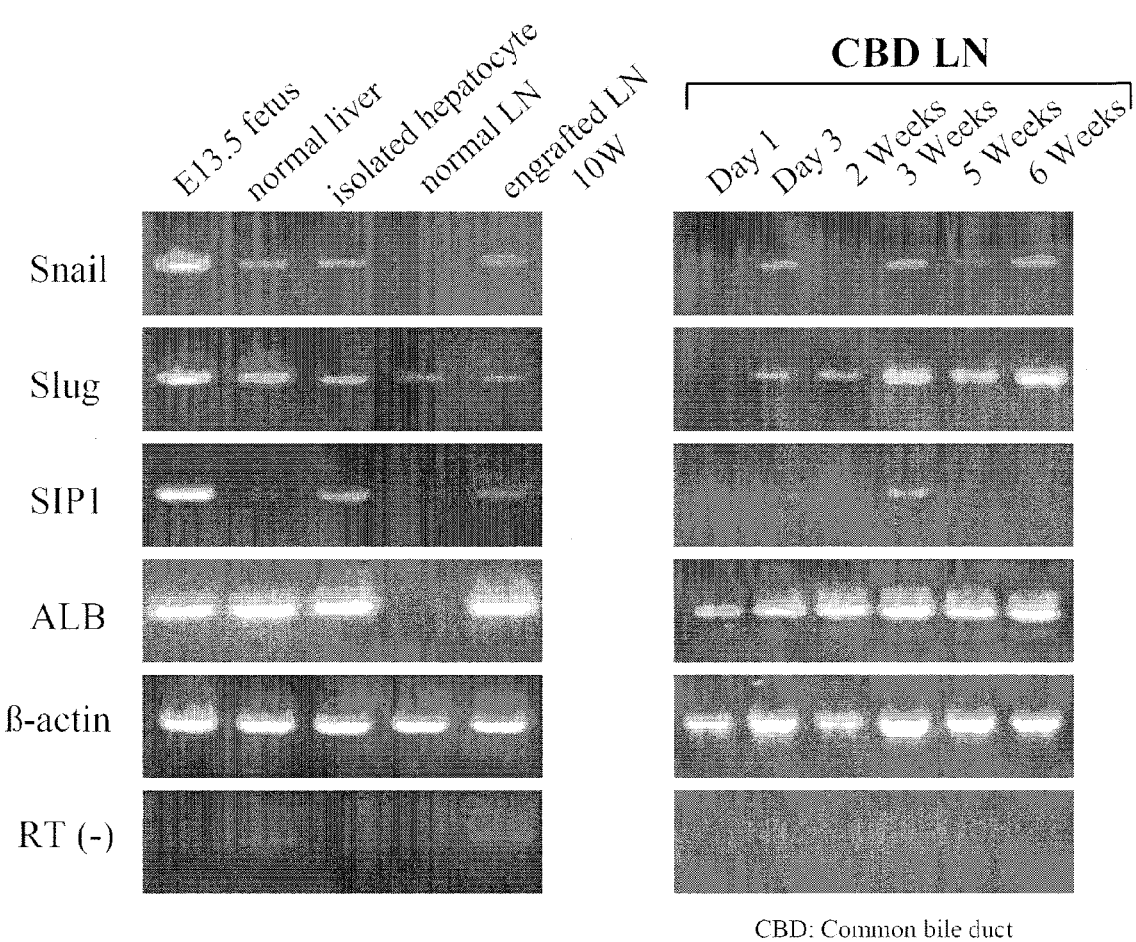
FIG. 14 shows RT-PCR of transcription factors with lymph nodes after intraperitoneal (IP) injection. The expression of Snail and albumin transcript could not be detected in normal lymph node. On day 1 after IP injection, albumin expression is detected in lymph node. Both, the expression of Snail and Slug gradually increased with albumin expression. CBD LN, common bile duct lymph node.

Transcription factors, which induce epithelial-mesenchymal transition (EMT) on lymph nodes after IP Injection: The panel of RT-PCR (FIG. 14). The expression of Snail and albumin transcript could not be detected in normal lymph node. On day 1 after IP injection, albumin expression is detected in lymph node. Both, the expression of Snail and Slug gradually increased with albumin expression.

Transmission electron microscopy. To confirm whether engrafted cells were functional mature hepatocytes, transmission electron microscopy was used to examine the ultrastructures of the cells in nodules (FIGS. 9A-9C). The cells in nodules contained many mitochondria, peroxisomes, and tight junctions with desmosomes; and formed biliary conaliculi with microvilli. All of these features are compatible with those of mature hepatocytes. Additionally, some non-fenestrated endothelial cells could be observed.

FAH enzyme assay. To estimate how much the nodules and the native liver from IP injected mice contribute to their whole liver function, an FAH enzyme assay was performed (Table 1, where n=4).

that is essential to recover from liver failure and to rescue FAH$^{-/-}$ mice. Interestingly, the FAH enzyme activity in native liver was near that of FAH$^{-/-}$ mice in 1 out of 4 cases and this indicated that no detectable transplanted hepatocytes engrafted in this native liver. This case suggested that only nodules contributed to the whole FAH enzyme activities.

Figure 10A:
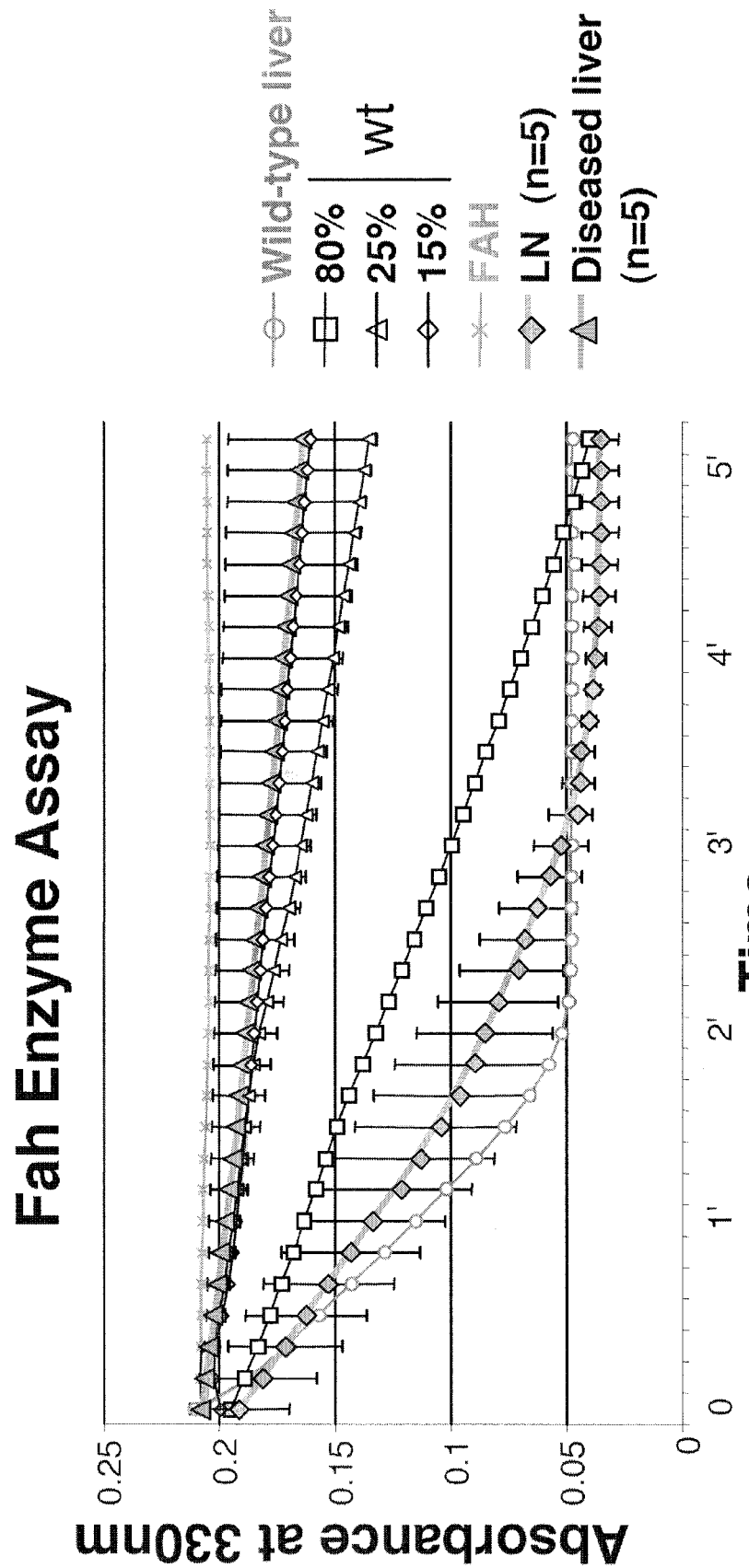
FIGS. 10A-10C shows FAH enzyme assay of the hepatic tissues and re-transplantation of lymph nodes derived hepatocytes.
Figure 13A:
FIGS. 13A-13H show the results of direct injection of wild-type liver cells into a single mesenteric lymph node.
Figure 13B:
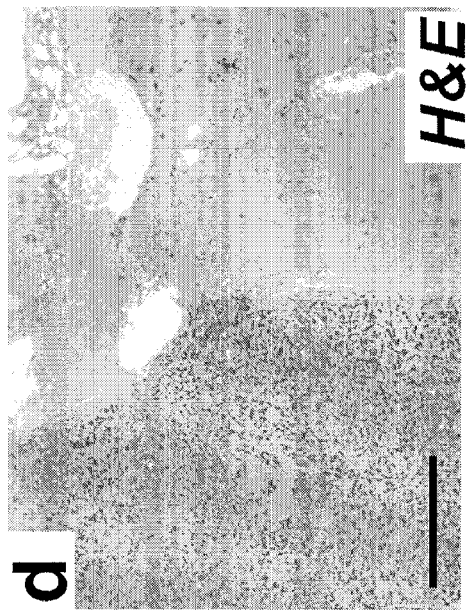
Figure 13C:
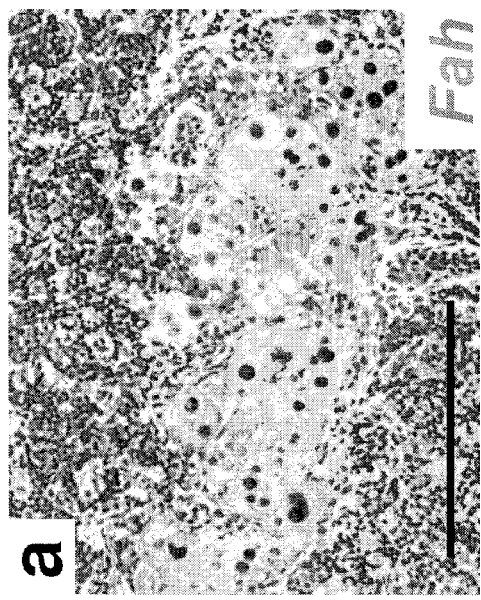
Figure 13D:
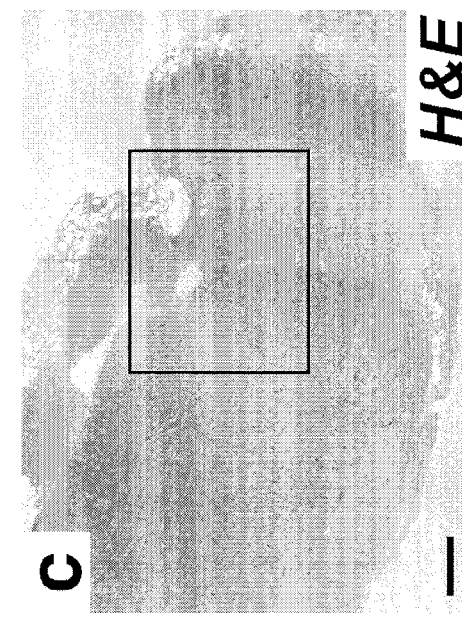
Figure 13E:
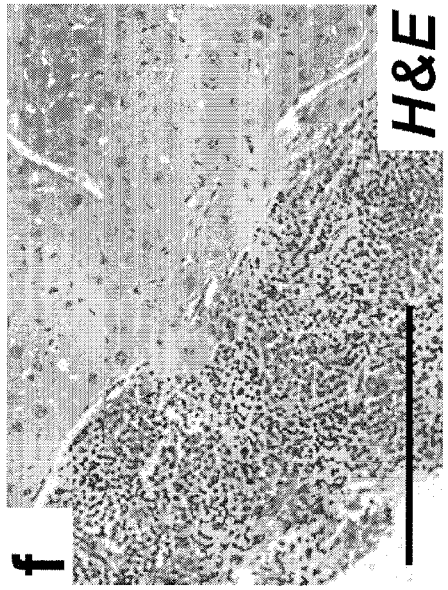
Figure 13F:
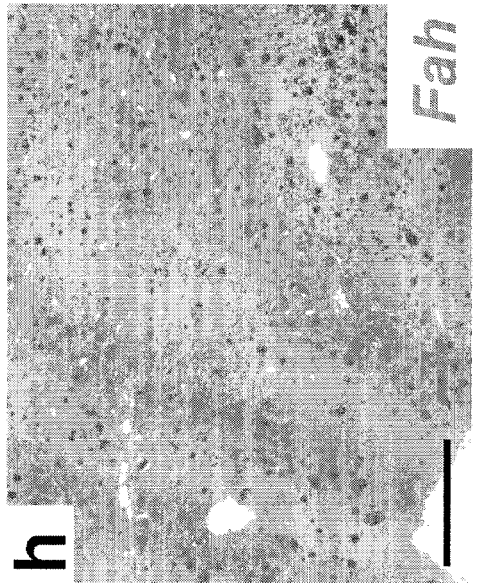

Occasionally, FAH immunostaining identified small intrahepatic nodules of donor hepatocytes in native tyrosinemic livers of IP injected mice (FIG. 2 and FIG. 13B). FAH enzyme activity was measured in order to estimate the number of donor hepatocytes in the native liver versus hepatic lymph nodes, and their contribution to the restoration of liver function, (FIG. 10A). FAH enzyme activities in hepatic lymph nodes ranged from 80% to almost 100% of wild-type liver levels. In contrast, FAH enzyme activities in native tyrosinemic liver had a mean activity close to 15% of wild-type liver levels. In 1 out of 5 cases, no trace FAH enzyme activity was detected in the native tyrosinemic liver, a result comparable to untransplanted FAH$^{-/-}$ mice. This data indicate that hepatocytes in lymphatic nodules contribute solely to the restoration of hepatic function.

Figure 10B:
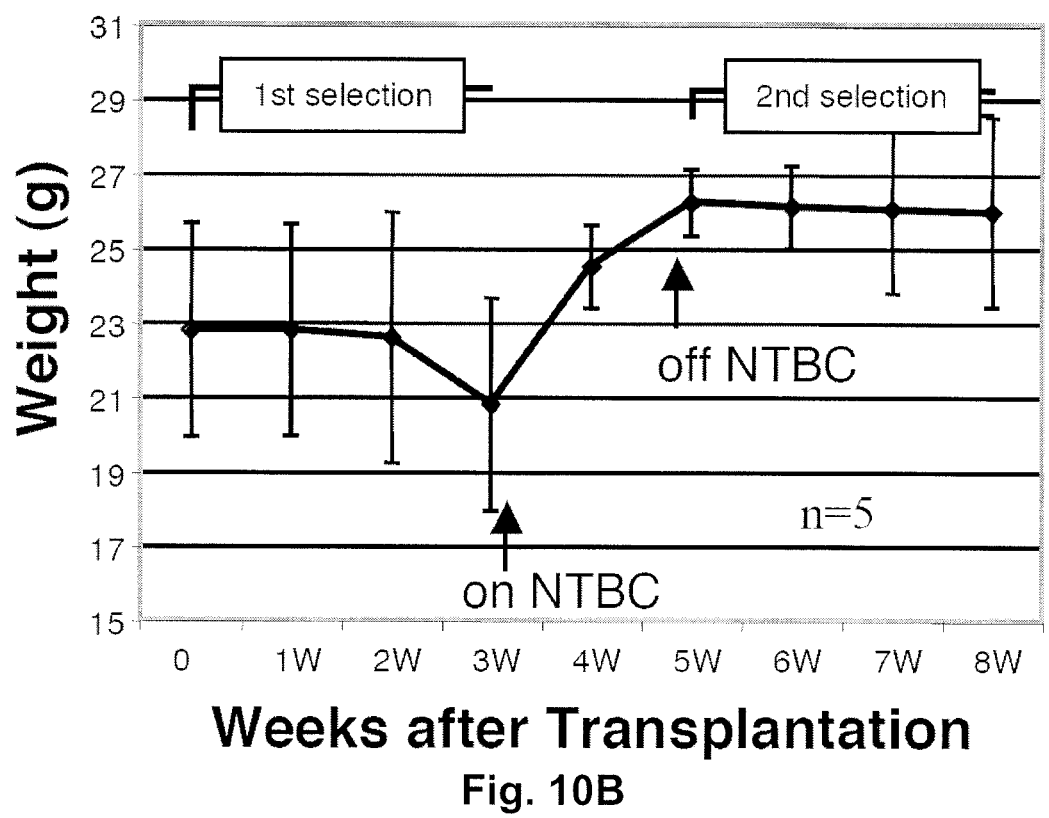
Figure 10C:
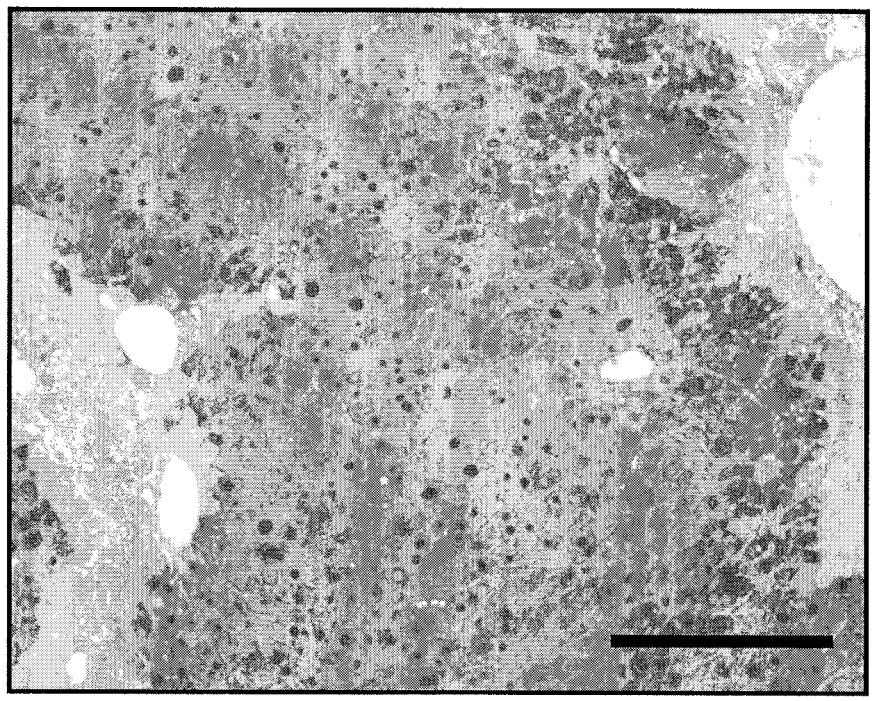

Re-transplantation of cells from nodules. To determine whether FAH positive hepatocytes in nodules were fully functional, cells were isolated from these nodules and transplanted intrasplenically into FAH$^{-/-}$ mice again. Mice were returned to NTBC treatment 4 weeks after transplantation. Eventually animals returned to their preoperative weight under the second selection (FIG. 10B). FAH staining showed that FAH positive hepatocytes engrafted and entirely repopulated in the liver (FIG. 10C). These results indicated that the cells in the nodules were fully functional hepatocytes and can rescue FAH$^{-/-}$ mice.

To examine how and when transplanted hepatocytes generate nodules, lymph nodes of stomach, common bile duct, spleen and mesenterium were harvested one and three days after IP injection. CK18 was used to identify hepatocytes. Some CK18 positive cells could be observed in the lymph nodes of the stomach and common bile duct on day 3. The degree of migration was varied among lymph nodes. Some lymph nodes had a cluster of CK18 positive cells (FIG. 5D and F) and others had a few CK18 positive cells in the periphery of lymph node (FIG. 5E and G). These results indicated that IP injected hepatocytes migrated into lymph nodes within 3 days after transplantation, engrafted there and even-

TABLE 1

Results from biochemical measures of liver functions

| Liver function parameter | units | IP injection | SP injection | wild-type (donor) | FAH-/- under NTBC | untreated FAH-/- |
|---|---|---|---|---|---|---|
| ALT | U/L | 154.51 ± 51.14 (16) | 67.33 ± 36.54 (8) | 20.75 ± 2.94 (6) | 34.35 ± 15.41 (9) | 228.89 ± 215.35 (8) |
| Total bilirubin | mg/dl | 1.41 ± 1.44 (16) | 0.18 ± 0.04 (8) | 0.13 ± 0.04 (6) | 0.10 ± 0.03 (9) | 6.33 ± 2.57 (8) |
| Direct bilirubin | mg/dl | 1.15 ± 1.21 (16) | 0.04 ± 0.03 (8) | 0.02 ± 0.01 (6) | 0.02 ± 0.01 (9) | 5.76 ± 2.13 (8) |
| Tyrosine | μM | 758 ± 552 (16) | 366 ± 305 (8) | 198 ± 120 (6) | 1018 ± 590 (9) | 2090 ± 850 (6) |
| Phenylalanine | μM | 352 ± 160 (16) | 240 ± 152 (8) | 234 ± 137 (6) | 225 ± 71 (9) | 401 ± 306 (6) |
| Alanine | μM | 702 ± 427 (16) | 544 ± 481 (8) | 326 ± 86 (6) | 360 ± 136 (9) | 1103 ± 1002 (6) |
| Glycine | μM | 255 ± 187 (16) | 153 ± 110 (8) | 129 ± 83 (6) | 100 ± 60 (9) | 159 ± 87 (6) |
| Valine | μM | 201 ± 143 (16) | 149 ± 110 (8) | 124 ± 71 (6) | 93 ± 44 (9) | 132 ± 76 (6) |
| Glutamate | μM | 414 ± 199 (16) | 221 ± 93 (8) | 271 ± 31 (6) | 284 ± 96 (7) | 2618 ± 2517 (6) |

Figure 15A:
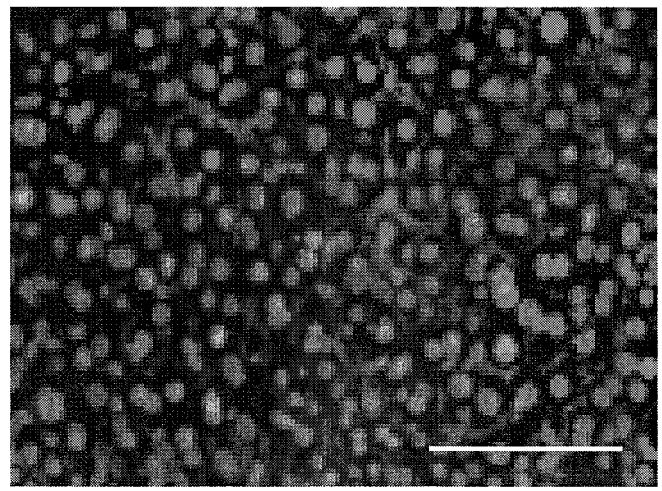
FIG. 15A shows a normal liver stained with slug in red and counterstained with DAPI.
Figure 15B:
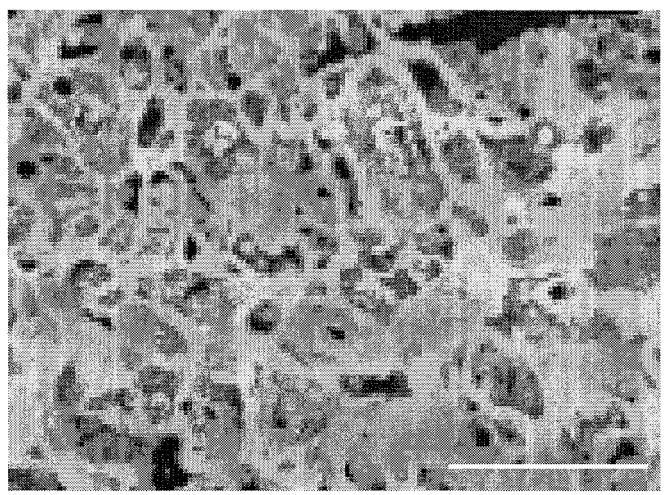
FIG. 15B shows a cross section of lymph node 3 weeks after IP transplantation. Hepatocytes are stained with cytokeratin 18 (green) and slug (red). The section is counterstained with DAPI.
Figure 15C:
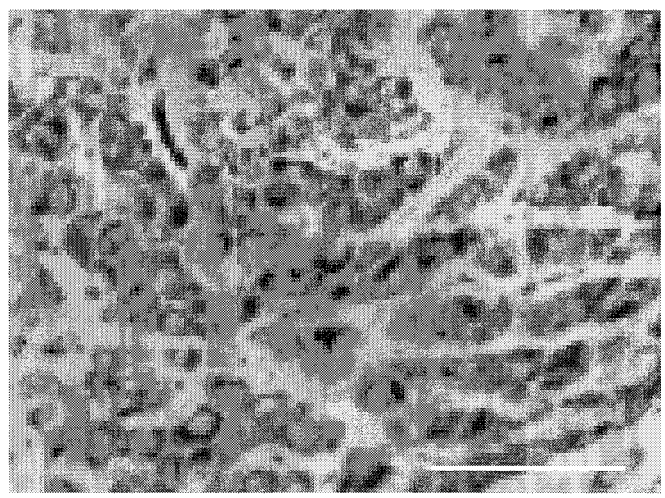
FIG. 15C shows a cross section of lymph node 10 weeks after IP transplantation. Hepatocytes are stained with cytokeratin 18 (green) and slug (red). The section is counterstained with DAPI.
Figure 16A:
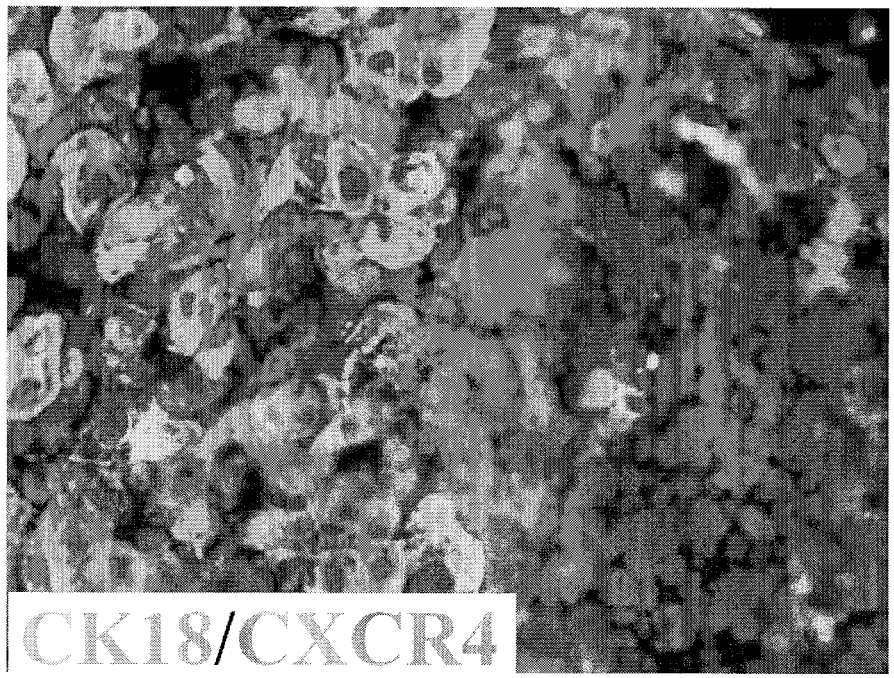
FIGS. 16A-16B are immunofluorescence photomicrographs showing immunostaining of CK18/CXCR4 and CCR7 in lymph nodes 3 days after IP injection. Both CXCR4 and CCR7 expression (red) are present in the lymph nodes early during hepatocyte (green) migration. Bar: 100 μm.
Figure 16B:
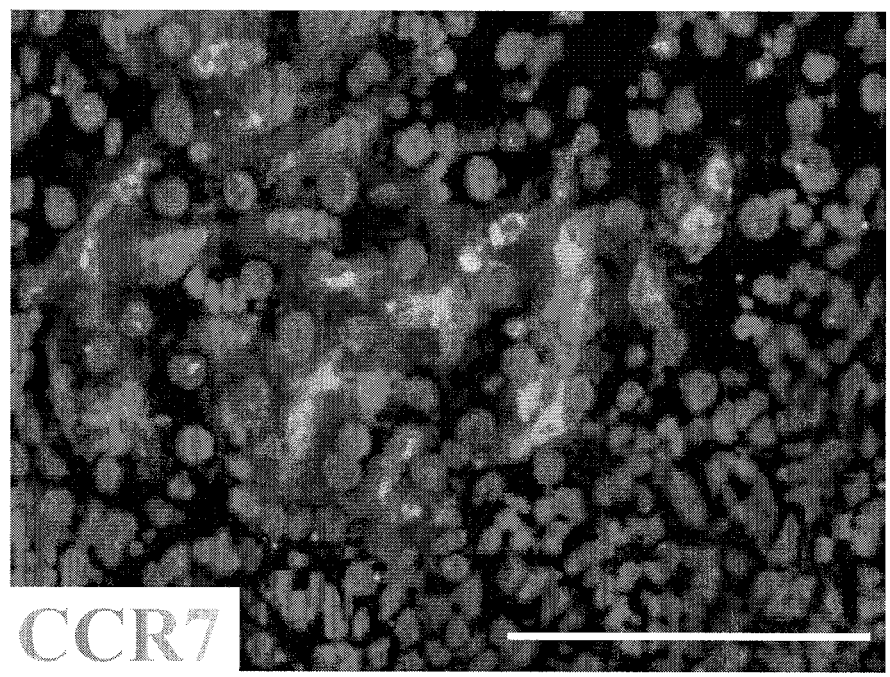

FAH enzyme activities in nodules ranged from 80% to almost 100% of wild-type liver levels. In contrast, FAH enzyme activities in native liver were less than 25% and the mean activity was very close to 15% of wild-type liver levels (FIG. 10A). Although it is unknown whether FAH enzyme activity can replicate the entire liver function, these results showed that these nodules had much of FAH enzyme activity tually generated small liver-like nodules. FIGS. 15A-C show immunohistochemical photomicrographs for normal liver (FIG. 15A), 3 weeks after IP injection (FIG. 15B), and 10 weeks after IP injection (FIG. 15C). Immunohistochemical stains are shown for Slug (red) and CK18 (green).

The lymph node architecture changed after transplantation and most of the cells in LNs were replaced by transplanted hepatocytes. HEVs, which are morphologically different from vessels in the liver, could not be observed anymore and the structure of CD31 positive vessels was very similar to the structure of normal liver. Additionally, F4/80 positive cells, (macrophage/Kupffer cells), were distributed in the similar manner of normal liver. These results suggested that the environment inside nodules changed to the similar environment of normal liver by the engrafted hepatocytes. Electron microscopy showed that blood vessels in nodules consisted of non-fenestrated endothelial cells, whereas endothelial cells in liver are fenestrated. Thus, it is possible that the endothelial cells of HEVs adapted to the new environment and changed their shape.

The overall survival rate of SP injection and IP injection was 90.4% and 80.0% respectively. Five out of seven dead IP injected mice were lost within 3 days after transplantation and extensive edematous intestine, probably due to the obstruction of the main branch of lymphatics on the mesenterium, could be found by autopsies. This indicates that transplanted hepatocytes can cause obstruction of lymphatics, resulting in extensive edematous intestine and death. Thus, the optimization of cell numbers and total volume transplanted can be used to further increase the safety of IP injections. On the other hand, IP injected mice needed to be put back on NTBC 4-5 weeks after transplantation. This suggests that the engraftment of hepatocytes under the first round of selection is not enough to rescue animals.

In general, the size of the liver is highly regulated by the functional needs of the organism. These experiments showed that the ratio of total weight of native liver and nodules against body weight (5.28±0.33%) was very close to the ratio of normal liver to body weight (4.19±0.60%). This result suggested that total liver mass in the body was highly controlled by the demand of liver function.

Once mice returned to their preoperative weight 8-10 weeks after transplantation, all of them kept the same weight and survived. Furthermore, the total liver mass was still maintained for 6 months after transplantation. Thus, cancerous transformation of the implanted cells was unlikely.

In these experiments, the immunohistochemistry data showed that no CK 19 positive cells could be clearly detected in nodules, although biliary canaliculi with microvilli could be observed on transmission electron microscopy. These results suggested that the network of biliary trees in nodules were possibly constructed, but was eventually disconnected from the intestine where produced bile juice should be excreted. Additionally, the chemical analysis showed both of total- and direct- bilirubin of IP injected mice were higher than normal levels.

Example 2

Lymph Nodes as a Site for Liver Regeneration

Figure 13G:
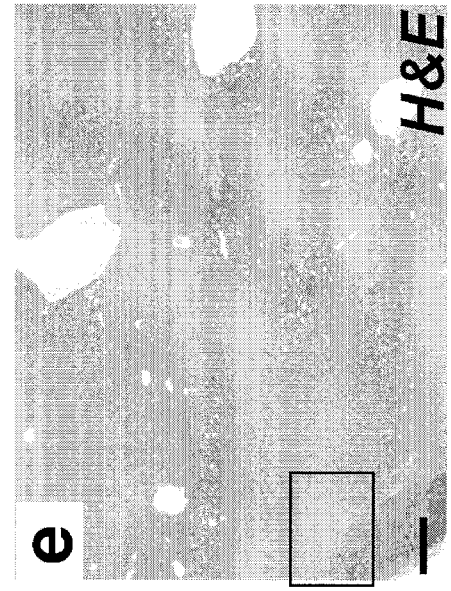
Figure 13H:
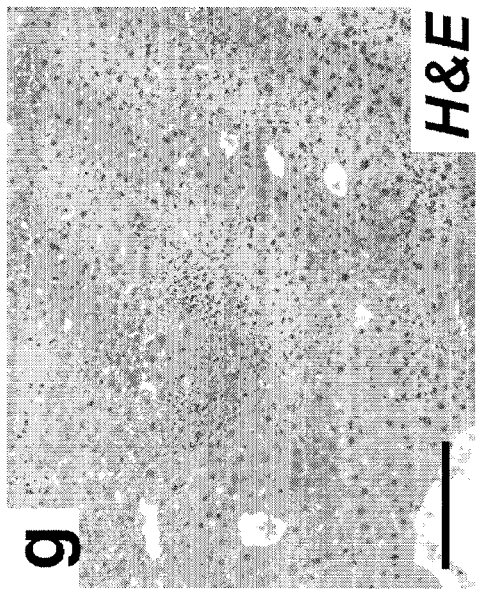

A single mesenteric node was injected in FAH$^{-/-}$ mice with $10^5$ wt liver cells. Ten days after removal of NTBC, a cluster of FAH$^+$ hepatocytes was identified in the injected lymph node. Three months later and after two cycles of selection, recipient mice were rescued from their lethal metabolic disorder. A single large hepatic lymph node was observed at the injection site (FIGS. 13A-13H). Histology and FAH staining confirmed the presence of donor hepatocytes. At 3 months after direct lymph node injection, 1.5×0.5×0.5 cm liver-like nodule could be observed at the injection site (FIG. 13B, circle). Most of engrafted cells were FAH positive (FIG. 13H) and the island of hematopoietic cells, reminiscent of the lymphatic system could be detected (FIGS. 13G, H). Therefore, direct transplantation of hepatocytes into a single lymph node could be a promising approach to site-specific ectopic liver generation.

In conclusion, the therapeutic efficacy of hepatic lymph nodes in restoring liver function represents a unique therapeutic approach to treat patients with end-stage liver disease. Furthermore, such an approach suggests that lymph nodes may be the preferred site for tissue engineering and regeneration of other tissues.

Example 3

Generation of Ectopic Liver in Lymph Nodes in the Context of an Allogeneic Barrier Described in this example are methods for generating ectopic liver in the lymph nodes, focusing on the context of the allogeneic barrier. The general response to an allogeneic barrier in hepatocyte transplantation is very sensitive and rejection to hepatocyte engraftment is fast. Minor histocompatibility differences between C57b1 (GFP) and 129sv (FAH) will prevent engrafting of GFP hepatocytes in FAH mice, where such histocompatibility differences are shown in Table 2.

TABLE 2

Histocompatibility differences between mouse strains C57b1 and 129sv.

| mouse strain | MHC haplotype | H-2K | I-Aα | I-Aβ | I-E | H-2D | H-2L | Qa-2 | Qa-1 | Vα TCR | Vβ TCR |
|---|---|---|---|---|---|---|---|---|---|---|---|
| C57b1 | b | b | b | b | — | b | — | a(+) | | a | b |
| 129sv | b | b | b | b | — | b | — | a(hi) | | b | b |

Figure 17A:
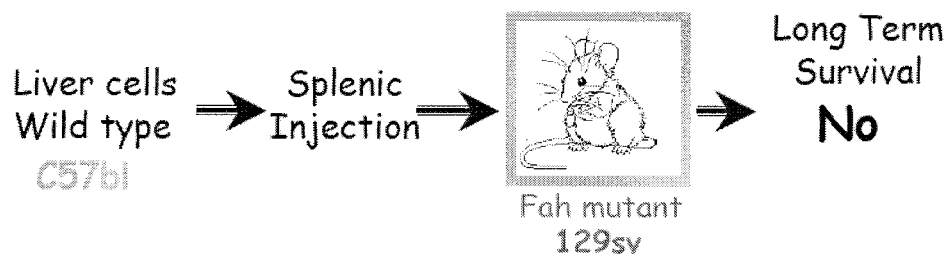
FIGS. 17A-17C shows the response to an allogeneic barrier in hepatocyte transplantation.
Figure 17B:
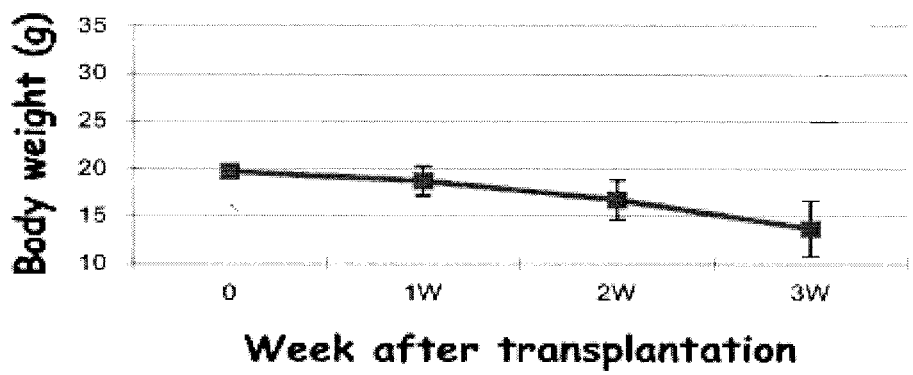
Figure 17C:
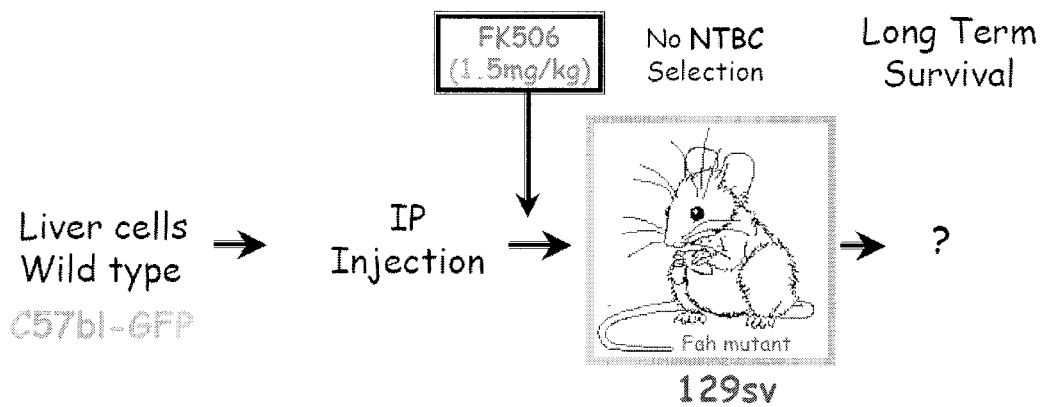

FIGS. 17A-17C show the response to an allogeneic barrier in hepatocyte transplantation. FIG. 17A is a schematic showing an experimental protocol for splenic injection of GFP-C57b1 wild type liver cells into an FAH mutant mouse (129sv), which does not lead to long term survival. FIG. 17B shows the change in body weight after transplantation of C57b1 hepatocytes (100,000 liver cells) by splenic injection into 129sv FAH mice (n=5). Three weeks after transplantation, all 5 mice died with no trace of engrafted GFP positive hepatocytes.

Figure 18:
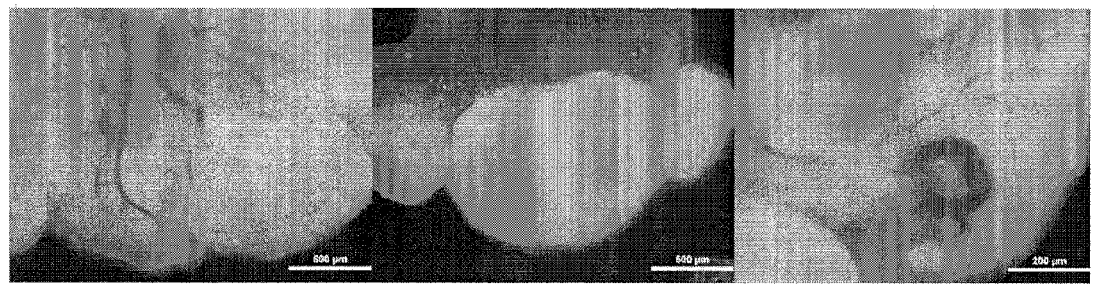
FIG. 18 are fluorescence microphotographs of GFP positive ectopic liver in FAH mice, where GFP-hepatocytes are shown in lymph nodes. Scale bars represent 500 μm.

FIG. 17C is a schematic showing an experimental protocol for splenic injection of GFP-C57b1 wild type liver cells into an FAH mutant mouse (129sv) with an immunosuppressive agent (FK506). FAH 129sv mice were treated with immunosuppressive drug FK506 (1.5 mg/kg) and then transplanted with IP injection of GFP hepatocytes (100,000 C57B1 liver cells). Whereas all five mice under the protocol of FIG. 17A died within 3 weeks, mice under the protocol of FIG. 17C were alive after 9 weeks. Though all five mice under the protocol of FIG. 17A did not have any engrafted GFP positive hepatocytes, the use of an immunosuppressive drug (FK506) generated allogeneic liver in lymph nodes. FIG. 18 shows fluorescence photomicrographs of GFP positive ectopic livers were isolated from the 129sv FAH mice (nine weeks after transplantation).

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed. Having described this invention, it will be understood to those of ordinary skill in the art that the same can be performed within a wide and equivalent range of conditions, formulations and other parameters without affecting the scope of the invention or any embodiment thereof.

Variations in the embodiments described in these parts would be apparent to those of skill in the art and such variants are intended to be included in what applicants' believe to be the inventions described herein.

I claim:

1. A method of producing ectopic liver tissue in a lymph node comprising introducing a therapeutically effective amount of hepatocytes into a lymph node of a subject with hepatic insufficiency and expanding the hepatocytes in the lymph node to produce ectopic liver tissue in the lymph node that supplements or replaces liver function in the subject.

2. The method of claim 1, where the lymph node is selected from the group consisting of the splenic hilar lymph node, celiac lymph node, porta hepatis lymph node, iliac lymph node, paraaortic lymph node, retroperitoneal lymph node, mesenteric lymph node, abdominal lymph node, and any combinations thereof.

3. The method of claim 1, wherein the hepatocytes are syngeneic to the lymph node.

4. The method of claim 1, wherein the hepatocytes are allogeneic to the lymph node.

5. The method of claim 1, wherein the hepatocytes are injected into a lymph node of a mammal.

6. The method of claim 1, wherein the hepatocytes are produced by a process of cellular re-programming.

7. The method of claim 1, wherein the hepatocytes are produced by differentiated stem cells.

8. The method of claim 1, wherein the hepatocytes are injected at a concentration range of $10^4$ to $10^{11}$ cells per lymph node.

9. The method of claim 8, wherein the concentration range is $10^5$ to $10^{10}$ cells per lymph node.

10. The method of claim 5, wherein the mammal has liver disease.

11. The method of claim 10, wherein the hepatocytes engraft.

12. The method of claim 11, wherein the graft rescues the mammal from liver disease.

13. The method of claim 1, wherein the hepatocytes are injected into a lymph node of a human.

14. The method of claim 5, wherein the hepatocytes are injected more than once.

15. The method of claim 5, wherein the mammal is treated to induce immunosuppression.

16. The method of claim 5, wherein the hepatocytes are human and the mammal is non-human.

17. The method of claim 10, wherein injecting the hepatocytes into a lymph node improves one or more liver function parameters in the mammal.

18. The method of claim 17, wherein the liver function parameter that is improved is one or more of ALT level, AST level, creatinine level, total bilirubin level, direct bilirubin level, phenylalanine level, alanine level, glycine level, valine level, and glutamate level.

19. A method of producing ectopic liver tissue in a lymph node comprising introducing $10^4$ to $10^{11}$ hepatocytes into a lymph node of a subject with hepatic insufficiency and expanding the hepatocytes in the lymph node to produce ectopic liver tissue in the lymph node that supplements or replaces liver function in the subject.

\* \* \* \* \*